(12) United States Patent
Sasson et al.

(10) Patent No.: US 9,409,904 B2
(45) Date of Patent: Aug. 9, 2016

(54) COMPOUNDS AND COMPOSITIONS FOR USE IN AUGMENTATION OF GLUCOSE

(75) Inventors: Shlomo Sasson, Jerusalem (IL); Erol Cerasi, Jerusalem (IL); Arie Lev Gruzman, Jerusalem (IL); Ella Meltzer-Mats, Rishon-LeZion (IL)

(73) Assignees: YISSUM RESEARCH DEVELOPMENT COMPANY OF THE HEBREW UNIVERSITY OF JERUSALEM LTD, Jerusalem (IL); DIAB R&D 1, Paris (FR); BAR ILAN UNIVERSITY, Ramat Gan (IL)

( * ) Notice: Subject to any disclaimer, the term of this patent is extended or adjusted under 35 U.S.C. 154(b) by 29 days.

(21) Appl. No.: 14/236,224

(22) PCT Filed: Aug. 1, 2012

(86) PCT No.: PCT/IL2012/050285
§ 371 (c)(1),
(2), (4) Date: Aug. 8, 2014

(87) PCT Pub. No.: WO2013/018095
PCT Pub. Date: Feb. 7, 2013

(65) Prior Publication Data
US 2015/0025094 A1 Jan. 22, 2015

Related U.S. Application Data

(60) Provisional application No. 61/513,802, filed on Aug. 1, 2011.

(51) Int. Cl.
| | |
|---|---|
| C07D 311/58 | (2006.01) |
| C07D 339/02 | (2006.01) |
| C07D 339/08 | (2006.01) |
| C07D 471/04 | (2006.01) |
| C07D 235/28 | (2006.01) |
| C07D 417/12 | (2006.01) |
| C07D 277/74 | (2006.01) |
| C07D 277/78 | (2006.01) |
| C07D 233/88 | (2006.01) |
| C07D 239/38 | (2006.01) |
| C07D 249/12 | (2006.01) |
| C07D 277/54 | (2006.01) |
| C07D 277/82 | (2006.01) |
| C07D 285/135 | (2006.01) |

(52) U.S. Cl.
CPC ............ *C07D 471/04* (2013.01); *C07D 233/88* (2013.01); *C07D 235/28* (2013.01); *C07D 239/38* (2013.01); *C07D 249/12* (2013.01); *C07D 277/54* (2013.01); *C07D 277/74* (2013.01); *C07D 277/78* (2013.01); *C07D 277/82* (2013.01); *C07D 285/135* (2013.01); *C07D 311/58* (2013.01); *C07D 339/02* (2013.01); *C07D 339/08* (2013.01); *C07D 417/12* (2013.01)

(58) Field of Classification Search
USPC .................................. 549/11, 362, 365, 406
See application file for complete search history.

(56) References Cited

U.S. PATENT DOCUMENTS

| 2,777,853 A | 1/1957 | Norbert Steiger | |
|---|---|---|---|
| 4,073,797 A * | 2/1978 | Ramuz .................... | C07C 45/46 549/20 |
| 4,325,959 A | 4/1982 | Matthews | |
| 7,812,142 B2 | 10/2010 | Sasson et al. | |

FOREIGN PATENT DOCUMENTS

| EP | 0555769 A2 | 8/1993 |
|---|---|---|
| EP | 0714893 A1 | 6/1996 |

(Continued)

OTHER PUBLICATIONS

Chemical Abstracts Registry No. 857020-67-8, indexed in the Registry file on STN CAS Online Jul. 26, 2005.*
Chemical Abstracts Registry No. 773101-55-6, indexed in the Registry file on STN CAS Online Nov. 1, 2004.*
Capilla et al., Synthetic Communications, 1996, 26(9), pp. 1729-1738.*
Prill et al., CA 51:7180, 1957.*

(Continued)

*Primary Examiner* — Laura L. Stockton
(74) *Attorney, Agent, or Firm* — Browdy and Neimark, PLLC

(57) ABSTRACT

The present invention is directed to compounds such as: formula wherein linker is independently selected from the group consisting of —S—, —S—S—, —S—(CH2)n-, —NH—, —NH—(CH2)n-, —O—, —SO2-, arylene, heteroarylene; R1 is selected from the group consisting of straight or branched C4-C20 alkyl, straight or branched C4-C20 alkenyl, straight or branched C4-C20 alkynyl, each optionally interrupted with at least one NH, C5-C7 saturated cycloalkyl or heteroalkyl ring, C5-C12 aromatic or heteroaromatic ring, each optionally substituted with at least one group selected from —COOH, —NH2, C1-C8 alkoxy, C1-C5 amidyle, C1-C5 carboxyl, halogen; and R2 is independently selected from the group consisting of H, OH, SH, NH2, NO2, halogen, CN, C1-C8 alkoxy, C1-C5 carboxylic acid, straight or branched C1-C8 alkyl, straight or branched C2-C10 alkenyl, straight or branched C2-C12 alkynyl each optionally substituted by at least one substituent selected from the group consisting of C1-C5 alkoxy, C1-C5 carboxylic acid, OH, SH, NH2, halogen; and compositions for use in the treatment of diabetes and related dis¬ orders.

(V)

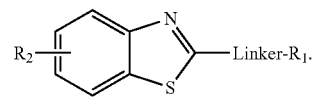

9 Claims, 15 Drawing Sheets

(56) References Cited

FOREIGN PATENT DOCUMENTS

| WO | 9635681 | A1 | 11/1996 |
| WO | 2004089470 | A2 | 10/2004 |
| WO | 2006094235 | A1 | 9/2006 |
| WO | 2008089462 | A2 | 7/2008 |

OTHER PUBLICATIONS

Prill et al., Contributions from Boyce Thompson Institute, 1955, vol. 18, pp. 187-192.*

Woltersdorf et al "Topically Active Carbonic Anhydrase Inhibitors. 1, 0 -Acyl Derivatives of 6-Hydroxybenzot hiazole-2-sulfonamide" J. Med. Chem 32 : 2486-2492 (1989).

Database Registry [Online] 1-7,9 Chemical Abstracts Servi Ce, Columbus, Ohio, US; Dec. 8, 2004, Chemical Library; Supplier: Enamine: XP002686540, Database accession No. 794538-56-0 abstract; XP002686540.

Database Registry [Online] Chemical Abstracts Service, Columbus, Ohio, US;Sep. 19, 2002, Chemical Library; Supplier: Ambinter: XP002686541, Database accession No. 452942-47-1 abstract; XP002686541.

Sepulveda et al "Inhibition of arenavirus infrection by thiuram and aromatic disulfides" Antiviral Research 87:329-337 (2010).

Giampietro et al "Synthesis and biological evaluation of 2-Heteroarylthioalkanoic Acid Analogues of Clofibric Acid as Peroxisome Proliferator-Activated Receptor or Agonists" Journal of Medicinal Chemistry Article. 52 : 6224-6232 (2009).

Chiba, "Effect of Sulfur-containing Compounds on Experimental Diabetes. VI. Screening of Hypoglycemic Action of Sulfur-containing Compounds" UDC 89: 1138-1142(1969).

Suter et al "Benzothiazoles as eventual oral antidiabetic drugs" Helvetica Chimica Acta, No. 4, pp. 1084-1086 (1967).

Meltzer-Mats et al "Synthesis and Mechanism of Hypoglycemic Activity of Benzothiazole Derivatives" Journal of Medicinal Chemistry 56 : 5335-5350 (Jan. 2013).

Merglen et al "Glucose Sensitivity and Metabolism-Secretion Coupling Studied during Two-Year Continuous Culture in INS-1E Insulinoma Cells" Endocrinology 145(2) 667-678 (2004).

Pasternak et al "Benzothiazole derivatives augment glucose uptake in skeletal muscle cells and stimulate insulin secretion from pancreatic b-cells via AMPK activation†" Chem Comm, The Royal Society of Chemistry 50: 11222-11225 (2014).

* cited by examiner

COMPOUNDS AND COMPOSITIONS FOR USE IN AUGMENTATION OF GLUCOSE

TECHNOLOGICAL FIELD

The present application is directed to compounds, compositions for use in the treatment of diabetes and related disorders.

BACKGROUND

Diabetes is a disease associated with high levels of sugar in the blood and is classified as Type 1 diabetes in which, the body makes little or no insulin or Type 2 diabetes. Type II diabetes is responsible for most of diabetes cases and is also associated with of high obesity rates. Diabetes affects more than 20 million Americans. Over 40 million Americans have pre-diabetes (early type 2 diabetes). The high blood sugar levels can cause several symptoms, including blurry vision, excess thirst, fatigue etc. A major pathophysiological factor in Type II diabetes is decreased glucose utilization in peripheral tissues, such as skeletal muscles and fat depots. Several clinical observations in diabetic patients suggest that hyperglycemia per se may contribute and even worsen this phenomenon. Current pharmacological treatments of type 2 diabetes include mono- and combination therapies of various oral antidiabetic drugs. In many cases these therapies fail to achieve optimal glycemic control.

Thus, there is a need to develop novel antihyperglycemic drugs, including those that are capable of augmenting the insulin secretory capacity of β-cells and/or increase the rate of glucose uptake in insulin sensitive tissues.

General Description

The present invention provides a compound having the general formula (I):

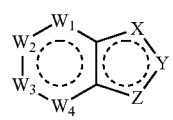
(I)

wherein

X, Y, Z are each independently selected from the group consisting of N, S, O, CH, C—SH, NH, N-linker-$R_1$, C-linker-$R_1$;

$W_1$, $W_2$, $W_3$, $W_4$ are each independently selected from the group consisting of N, $CR_2$;

linker is independently selected from the group consisting of —S—, —S—S—, —S—$(CH_2)_n$—, —NH—, —NH—$(CH_2)_n$—, —O—, —$SO_2$—, arylene, heteroarylene;

n is 1 to 5;

$R_1$ is selected from the group consisting of straight or branched $C_4$-$C_{20}$ alkyl, straight or branched $C_4$-$C_{20}$ alkenyl, straight or branched $C_4$-$C_{20}$ alkynyl, each optionally interrupted with at least one NH, $C_5$-$C_7$ saturated cycloalkyl or $C_5$-$C_7$ heteroalkyl ring, $C_5$-$C_{12}$ aromatic or heteroaromatic ring, each optionally substituted with at least one group selected from —COOH, —$NH_2$, $C_1$-$C_8$ alkoxy, $C_1$-$C_5$ amidyle, $C_1$-$C_5$ carboxyl, halogen;

$R_2$ is independently selected from the group consisting of H, OH, SH, $NH_2$, $NO_2$, halogen, CN, $C_1$-$C_8$ alkoxy, $C_1$-$C_5$ carboxylic acid, straight or branched $C_1$-$C_8$ alkyl, straight or branched $C_2$-$C_{10}$ alkenyl, straight or branched $C_2$-$C_{12}$ alkynyl each optionally substituted by at least one substituent selected from the group consisting of $C_1$-$C_5$ alkoxy, $C_1$-$C_5$ carboxylic acid, OH, SH, $NH_2$, halogen;

provided that at least one of X, Y, and Z is selected from N-linker-$R_1$ or C-linker-$R_1$.

In some embodiments, the alkyl, alkenyl and alkynyl may be optionally interrupted with one or more oxygen, sulfur, including S(=O) and S(=O)$_2$ groups, or NH group along the carbon chain, in some further embodiments the alkyl, alkenyl and alkynyl may be optionally interrupted with at least one NH group.

In yet some further embodiments, the alkyl, alkenyl and alkynyl may be optionally substituted by $C_1$-$C_5$ alkoxy, $C_1$-$C_5$ carboxylic acid, OH, SH, $NH_2$, halogen.

In some embodiments, the $C_5$-$C_7$ saturated cycloalkyl or $C_5$-$C_7$ heteroalkyl ring, $C_5$-$C_{12}$ aromatic or heteroaromatic ring may be substituted with one or more substituents, in certain embodiments one, two, three or four substituents, where the substituents are selected from —COOH, —$NH_2$, $C_1$-$C_8$ alkoxy, $C_1$-$C_5$ amidyle, $C_1$-$C_5$ carboxyl, halogen.

In some embodiments X and Z are each independently N or S. In some further embodiments, Y is N-linker-$R_1$ or C-linker-$R_1$. In some yet further embodiments, Y is C-linker-$R_1$.

In some embodiments, the linker is —S—$(CH_2)_n$—, —NH—$(CH_2)_n$—. According to these embodiments, the group —$(CH_2)_n$— wherein n=1 to 5, may encompasses an alkyl, alkenyl and alkynyl as defined herein having at most five carbon atoms. In yet some further embodiments, the linker is —S—S—, —S—$CH_2$—.

In some embodiments, $R_1$ is straight or branched $C_4$-$C_{20}$ alkyl, straight or branched $C_4$-$C_{20}$ alkenyl, straight or branched $C_4$-$C_{20}$ alkynyl. In some embodiments, $R_1$ is optionally interrupted with at least one heteroatoms selected from O, S, or NH. In some further embodiments, $R_1$ is optionally interrupted with at least NH.

In some other embodiments, $R_1$ is $C_5$-$C_7$ saturated cycloalkyl or $C_5$-$C_7$ heteroalkyl ring, $C_5$-$C_{12}$ aromatic or heteroaromatic ring. In some embodiments, $R_1$ is benzothiazole. In some other embodiments, $R_1$ is 1,3-dioxane.

In such embodiments, $R_1$ is optionally substituted with at least one group selected from —COOH, —$NH_2$, $C_1$-$C_8$ alkoxy, $C_1$-$C_5$ amidyle, $C_1$-$C_5$ carboxyl, halogen. In some embodiments, the alkoxy group is an ethoxy group.

In some embodiments, $W_1$, $W_2$, $W_3$, $W_4$ are each independently N. In some embodiments, $W_1$, $W_2$, and $W_3$, are N and $W_4$ is $CR_2$, at times $W_1$, $W_2$, and $W_4$, are N and $W_3$ is $CR_2$, at times $W_1$, $W_3$, and $W_4$, are N and $W_2$ is $CR_2$ and at times $W_2$, $W_3$, and $W_4$, are N and $W_1$ is $CR_2$.

In some further embodiments, each of $W_1$, $W_2$, $W_3$ and $W_4$ is independently $CR_2$. In these embodiments, $R_2$ may be H, OH, SH, $NH_2$, $NO_2$, halogen, CN, $C_1$-$C_8$ alkoxy, $C_1$-$C_5$ carboxylic acid. In some other embodiments, $R_2$ may be straight or branched $C_1$-$C_8$ alkyl, straight or branched $C_2$-$C_{10}$ alkenyl, straight or branched $C_2$-$C_{12}$ alkynyl. In these embodiments, $R_2$ may optionally substituted by at least one substituent selected from the group consisting of $C_1$-$C_5$ alkoxy, $C_1$-$C_5$ carboxylic acid, OH, SH, $NH_2$, halogen.

In some embodiments, $R_2$ is a $C_1$-$C_8$ alkoxy, at times an ethoxy group. In some other embodiments, $R_2$ is OH.

In some embodiments a compound of the invention has the general formula (V):

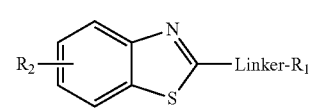
(V)

wherein $R_1$, Linker and $R_2$ are as defined hereinabove.

In further embodiments a compound of the invention has the general formula (VI):

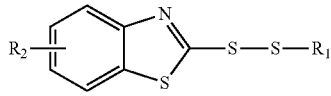

(VI)

wherein $R_1$ and $R_2$ are as defined hereinabove.

In other embodiments a compound of the invention has the general formula (VII):

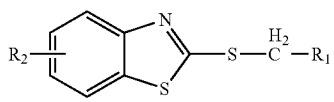

(VII)

wherein $R_1$ and $R_2$ are as defined hereinabove.

In accordance with this aspect, the invention also provides a compound selected from the following list:

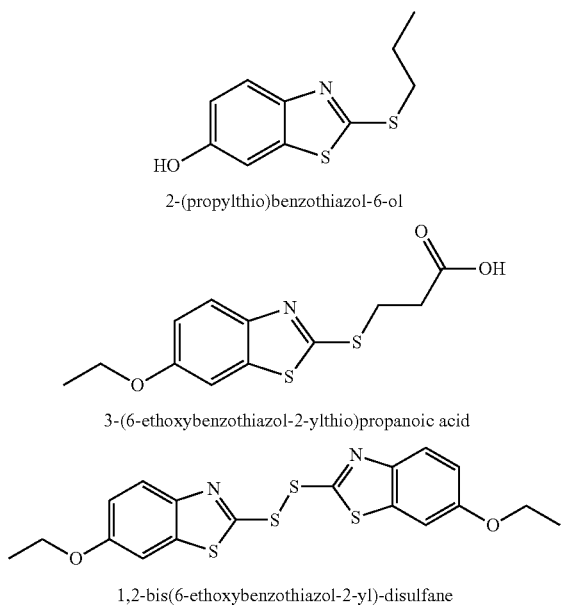

2-(propylthio)benzothiazol-6-ol 3-(6-ethoxybenzothiazol-2-ylthio)propanoic acid 1,2-bis(6-ethoxybenzothiazol-2-yl)-disulfane 2-((6-ethoxybenzothiazol-2-yl)thio)-N-propylacetamide 2-(Benzothiazol-2-ylmethylsulfanyl)-6-ethoxy-benzothiazole

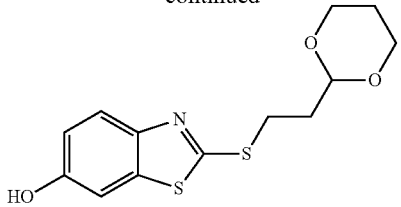

2-(2-[1,3]Dioxan-2-yl-ethylsulfanyl)-benzothiazol-6-ol

The present invention provides in accordance with a second aspect a compound having the general formula (II):

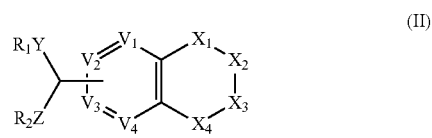

(II)

wherein $X_1, X_2, X_3$ and $X_4$ are each independently selected from the group consisting of S, O, $CH_2$, $CHR_3$, NH, $NR_3$; provided that at least one of $X_1$ to $X_4$ is O or S;

$V_1, V_2, V_3$ and $V_4$ are each independently selected from N, C, CH and $CR_4$;

Y and Z are each independently S or O;

$R_1$ and $R_2$ are each independently selected from straight or branched $C_1$-$C_{20}$ alkyl, straight or branched $C_2$-$C_{20}$ alkenyl, straight or branched $C_2$-$C_{20}$ alkynyl, each optionally interrupted with at least one NH; or wherein $R_1$ and $R_2$ together with Y, Z and the carbon atom connecting them a 5 to 10 membered ring; optionally substituted by at least one group selected from straight or branched $C_1$-$C_{10}$, alkyl, straight or branched $C_2$-$C_{10}$ alkenyl, straight or branched $C_2$-$C_{10}$ alkynyl;

$R_4$ is selected from the group consisting of halogen, straight or branched $C_1$-$C_{20}$ alkyl, straight or branched $C_2$-$C_{20}$ alkenyl, straight or branched $C_2$-$C_{20}$ alkynyl;

$R_3$ is selected from the group consisting of straight or branched $C_1$-$C_{12}$ alkyl, straight or branched $C_2$-$C_5$ alkenyl, straight or branched $C_2$-$C_5$ alkynyl, —COOH, —$NH_2$, $C_1$-$C_8$ alkoxy, $C_1$-$C_5$ amidyle, $C_1$-$C_5$ carboxyl, $C_6$-$C_{12}$ aryl, $C_4$-$C_{12}$ heretroaryl and heterocyclyl, wherein each of aryl, heretroaryl and heterocyclyl is optionally substituted by at least one of alkoxy, alkyl, alkenyl, alkynyl, amino, cyano, halogen, and 1,3-dithian-benzyl.

In some embodiments, at least one of $X_1$ to $X_4$ is O or S, at some further embodiments at least two of $X_1$ to $X_4$ are O or S. In some other embodiments, at least one of $X_1$ to $X_4$ is O or $CHR_3$.

In some embodiments, $R_3$ may be straight or branched $C_1$-$C_{12}$ alkyl, straight or branched $C_2$-$C_5$ alkenyl, straight or branched $C_2$-$C_5$ alkynyl, —COOH, —$NH_2$, $C_1$-$C_8$ alkoxy, $C_1$-$C_5$ amidyle, $C_1$-$C_5$ carboxyl.

In some further embodiments, $R_3$ may be $C_6$-$C_{12}$ aryl, $C_4$-$C_{12}$ heretroaryl and heterocyclyl, wherein each of aryl, heretroaryl and heterocyclyl. In such embodiments, $R_3$ is optionally substituted by at least one of alkoxy, alkyl, alkenyl, alkynyl, amino, cyano, halogen, and 1,3-dithian-benzyl.

As used herein the term "$C_1$-$C_{20}$ alkyl" is meant to encompass straight or branched alkyl having 1 to 20 carbons, in some embodiments, contain from 4 to 20 carbons, in yet some embodiments from 1 to 8 carbons. As used herein the term "$C_2$-$C_{20}$ alkenyl" is meant to encompass a straight or branched alkenyl chain having between 2 to 20 carbon atoms, in some embodiments from 4 to 20 carbons, at some further embodiments from 2 to 10 carbons, and at least one double bond. As used herein the term "$C_2$-$C_{20}$ alkynyl" is meant to encompass a straight or branched alkynyl chain having between 2 to 20 carbon atoms, in certain embodiments, from 4 to 20 carbons, at some further embodiments, from 2 to 12 carbons, and at least one triple bond.

As used herein "alkoxy" refers to an alkyl group bonded to an oxygen atom. At times, the alkyl group may include one to eight carbon atoms, at times between one to five carbon atoms. Representative examples are methoxy, ethoxy, n-propoxy, isopropoxy, butoxy, sec-butoxy, tert-butoxy, pentoxy, isopentoxy, hexoxy, isohexoxy and the like. In certain embodiments, the alkoxy is ethoxy.

The term "halogen" (halo or halide) refers to F, Cl, Br or I.

As used herein, "$C_5$-$C_7$ saturated cycloalkyl" refers to a saturated mono- or multi-cyclic ring system having 5 to 7 carbon atoms. Example of "$C_5$-$C_7$ cycloalkyl" groups include, but are not limited to cyclopentyl, cyclohexyl and cycloheptyl.

As used herein, "heterocycloalkyl" refers to a monocyclic or multi-cyclic non-aromatic ring system having 5 to 7 members, where one or more, in certain embodiments, 1 to 3, of the atoms in the ring system is a heteroatom, that is, an element other than carbon, including but not limited to, nitrogen, oxygen or sulfur. Examples of "heteroalkyl" include, but are not limited to, pyran, 1,4-dioxane, 1,3-dioxane, piperidine, pyrrolidine, morpholine, tetrahydrothiopyran, tetrahydrothiophene, and the like.

As used herein, "$C_5$-$C_{12}$ aromatic" refers to aromatic ring systems having 5 to 12 carbon atoms, such as phenyl, naphthalene and the like.

As used herein, "$C_5$-$C_{12}$ heteroaromatic" refers to heteroaromatic ring systems containing one or more heteroatoms selected from nitrogen, oxygen and sulfur such as furan, thipohene, pyrrole, oxazole, thiazole, imidazole, pyrazole, isoxazole, thiazolem benzofurna, indole, benzothiophene, benzoimidazole, indazole, benzoxazole, benzoisoxazole, benzothiazole, isobenzfuran, isoidole, purine, pyridine, pyrazine, pyrimidine, pyrisazine, quinoline, quinozaline, quinazoline, isoquinoline.

As used herein, "arylene" refers to a monocyclic or polycyclic, in some embodiments monocyclic, divalent aromatic group, in one embodiment having from 5 to about 20 carbon atoms and at least one aromatic ring, in another embodiment 5 to 12 carbons. Arylene groups include, but are not limited to, 1,2-, 1,3- and 1,4-phenylene. In some embodiments, the arylene group is phenylene, in some further embodiments, the arylene is 1,4-phenylene.

As used herein, "heteroarylene" refers to a monocyclic refers to a divalent monocyclic or multicyclic aromatic ring system, in one embodiment of about 5 to about 15 atoms in the ring(s), where one or more, in certain embodiments 1 to 3, of the atoms in the ring system is a heteroatom, that is, an element other than carbon, including but not limited to, nitrogen, oxygen or sulfur.

As used herein, the term "substituted" refers to substitution with the named substituent or substituents, multiple degrees of substitution being allowed unless otherwise stated.

The term "$C_5$-$C_{12}$ aromatic ring" used interchangeably with the term "aryl" as used herein is intended to include carbocyclic aromatic ring systems having between 5 to 12 carbon atoms, such as for example phenyl, naphthyl.

The term "$C_4$-$C_{12}$ heteroaromatic" used interchangeably with the term "heteroaryl" as used herein is intended to include heterocyclic aromatic ring systems containing 4 to 12 carbon atoms and one or more heteroatoms selected from nitrogen, oxygen and sulfur such as furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzothiazolyl, benzoisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like.

As used herein, the term "heterocycloalkyl" or "heterocyclyl" or the term "heterocyclic" refers to a three to twelve-membered non-aromatic ring being unsaturated or having one or more degrees of unsaturation containing one or more heteroatomic substitutions selected from S, SO, $SO_2$, O, or N. "heterocyclic" ring(s) or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

The compounds of the present invention, as defined above, may have the ability to crystallize in more than one form, a characteristic, which is known as polymorphism, and it is understood that such polymorphic forms ("polymorphs") are within the scope of formulae (I). Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

Certain of the compounds described herein may contain one or more chiral atoms, or may otherwise be capable of existing as two enantiomers or as two or more diastereomers. Accordingly, the compounds of this invention include mixtures of enantiomers as well as purified enantiomers or enantiomerically enriched mixtures. Furthermore, the compounds of this invention include mixtures of diastereomers, as well as purified stereoisomers or diastereomerically enriched mixtures. Also included within the scope of the invention are the individual isomers of the compounds of the invention, as defined above, as well as any wholly or partially mixtures thereof. The present invention also covers the individual isomers of the compounds represented by the formulas above as mixtures with isomers thereof in which one or more chiral centers are inverted.

It is also noted that the compounds of the present invention may form tautomers. It is understood that all tautomers and mixtures of tautomers of the compounds of the present invention, are included within the scope of the compounds of the present invention.

In a further aspect, the invention provides a composition comprising a compound of general Formula (I), (II) (III), (IV), (V), (VI) or (VII) as defined herein above, or any salt thereof.

In some embodiments, said composition is a pharmaceutical composition, wherein said salt is a pharmaceutically acceptable salt.

Pharmaceutical compositions of the invention may additionally comprise any other suitable substances such as other therapeutically useful substances, diagnostically useful substances, pharmaceutically acceptable carriers or the like.

In some embodiments a compound or composition of the invention is administered (suitable to be administered) to an adipose tissue of a subject. In some embodiments said compound or composition of the invention is administered directly to an adipose tissue of a subject. In other embodiments said administration is via injection. In other embodiments, said administration is via a transdermal delivery device (for example a patch containing a compound or composition of the invention) at a close proximity to the adipose tissue location of said subject (for example the direct skin or mucosal tissue in contact with said adipose tissue).

Pharmaceutical compositions of the invention comprise a compound of the subject invention in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous, intra-adipose tissue and intradermal) administration or administration via an implant. The compositions may be prepared by any method well known in the art of pharmacy. Such methods include the step of bringing in association compounds used in the invention or combinations thereof with any auxiliary agent. The auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

In some embodiments, compositions of the invention include also compositions where the compound of the invention is formulated in a fat emulsion formulation (i.e. formulated in conventional formulation processes to produce an emulation comprising at least one fat component, either from a natural or synthetic source), such as for example Intralipid formulation (in any concentration).

The exact dose and regimen of administration of the composition will necessarily be dependent upon the therapeutic or nutritional effect to be achieved and may vary with the particular formula, the route of administration, and the age and condition of the individual subject to whom the composition is to be administered.

The invention also includes any salt of a compound of the invention, including any pharmaceutically acceptable salt, wherein a compound of the invention has a net charge (either positive or negative) and at least one counter ion (having a counter negative or positive charge) is added thereto to form said salt. The phrase "pharmaceutically acceptable salt(s)", as used herein, means those salts of compounds of the invention that are safe and effective for pharmaceutical use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, iso nicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts.

In another aspect there is provided a compound of the invention, as defined herein above, for use as a medicament.

In a further aspect the invention provides a use of a compound of the invention as defined herein above, for the preparation of a medicament.

In some embodiments, said medicament is for the treatment or prevention of a condition, symptom or disease associate with elevated blood glucose levels.

In a further aspect the invention provides a compound of the invention, for use in at least one of increasing the rate of glucose uptake and augment glucose-stimulated insulin secretion. In some embodiments, a compound of the invention is capable of increasing the rate of glucose uptake and augment glucose-stimulated insulin secretion.

In some embodiments, said medicament is for treating or preventing at least one condition selected from hyperglycemia, diabetes, altered insulin secretion, insulin resistance, cardiovascular disorders, obesity and the metabolic syndrome.

In certain embodiments, the condition is associated with hyperglycemia. In some embodiments, the condition is metabolic syndrome. Medical syndrome is a combination of medical disorders that increase the risk to develop cardiovascular disease and diabetes. Metabolic syndrome is also known as metabolic syndrome X, cardiometabolic syndrome, syndrome X and insulin resistance syndrome. In certain embodiments, the condition is associated with cardiovascular disorder.

In some embodiments, the condition is altered insulin secretion. In some other embodiments, the condition is insulin resistance. In some embodiments, the condition is diabetes.

As appreciated, diabetes often referred to as diabetes mellitus (DM) is considered as a group of metabolic diseases associated with high levels of glucose in the blood. At times, the high blood glucose is either due to the fact that the body does not produce enough insulin, or because cells do not respond to the insulin that is produced and secreted.

Type I diabetes mellitus (DM) (previously referred to as "insulin-dependent diabetes mellitus" (IDDM) is a result of the body's failure to produce insulin, and thus often requires the person to inject insulin or wear an insulin pump.

Type II DM (previously referred to as non insulin-dependent diabetes mellitus (NIDDM)) is a result of insulin resistance, in which cells fail to use insulin properly, sometimes combined with partial or an absolute insulin deficiency.

In addition, another type of diabetes is gestational diabetes, occurring in pregnant women without a previous diagnosis of diabetes and develops a high blood glucose level.

According to the present invention, the diabetes is Type I or Type II.

The inventors have found that the compounds developed herein increased the rate of glucose uptake in skeletal muscle cells (L6 myotubes). In addition, the compounds were shown to increase the abundance of glucose transporter-4 (GLUT4) in the plasma membrane of the myotubes. As appreciated, GLUT4 is the insulin-regulated glucose transporter found in adipose tissues and striated muscle (skeletal and cardiac) that is responsible for insulin-regulated glucose transport into the cell.

Without being bound by theory, the increased translocation of GLUT4 into the plasma membrane may be connected to the increased glucose uptake by the cells.

Thus, in some embodiments, the compounds described herein increase glucose uptake into the cells. In some other embodiments, the compounds described herein increase translocation of GLUT into the plasma membrane.

In was also found by the inventors that the increased rate of glucose uptake in some of the compounds was in an insulin-independent manner. Specifically, the inventors have shown that the novel compounds did not activate AKT/PKB, a key regulator on the insulin transduction pathway.

In skeletal muscles, activated Adenosine monophosphate-Activated Protein Kinase (AMPK) increases the rate of glucose transport and fatty acid oxidation, while in the liver it predominantly increases glucose uptake. These effects lead to increased peripheral glucose disposal and reduced blood glucose levels in hyperglycemic individuals. The enzyme AMPK, which acts as a sensor of cellular energy status, plays a central role in the regulation of glucose transport in skeletal muscles. Several AMPK isoenzymes have been identified, of which AMPKα2 is the abundant one in skeletal muscles. This enzyme is physiologically activated when the AMP:ATP ratio is increased in cells. Activated AMPK promotes the translocation of GLUT-4-containing vesicles to the plasma membrane in a non-insulin-dependent manner. Without wishing to be bound by theory, the compounds described herein were found to induce AMPK activation by inducing $Thr^{172}$ phosphorylation in AMPK. In some embodiments, the compounds described herein activate AMPK. Thus, these compounds were able to increase the rate of glucose entry to skeletal muscles, even under hyperglycemia conditions. Previously, two large groups of antidiabetic drugs (biguanides and thiazolidinediones) were found to be activators of AMPK. However, side effects, such as lactic acidosis, fluid retention, weight gain and development of tolerance to long-term use, emphasize the need for better tissue- and isoform specific AMPK activators. The compounds defined herein may improve the uptake of glucose into the cells and thus reduce the level of glucose in the blood.

In addition, the compounds defined herein were found to promote the increase of insulin secretion in β-cell in pancreatic islets of Langerhans. Specifically, the inventors have found that the compounds defined herein augments glucose-stimulated insulin secretion. Without being bound by theory, these compounds can use to increase the rate of glucose uptake in insulin sensitive tissues.

Thus, the compounds defined herein may be used as insulin secretagogues, namely triggering insulin secretion by direct action on the pancreatic β cells.

In addition, the inventors have found that compounds defined herein may possess dual function: on one hand they increase the rate of glucose uptake in skeletal muscle cells, and on the other hand, augment glucose-stimulated insulin secretion from cultured β-cells. Specifically, it was found by the inventors that both bis(6-ethoxybenzo[d]thiazol-2-yl)disulfane and 2-(propylthio)benso[d]thiazol-6-ol) have such dual function.

Without being bound by theory, the combination of increased insulin secretion and augmented glucose uptake in skeletal muscles may synergistically increase peripheral glucose disposal in hyperglycemic individuals. In certain embodiments, the condition is obesity.

The term "obesity" is meant to encompass is a condition in a subject having excess body fat. It is defined by body mass index (BMI) and further evaluated in terms of fat distribution via the waist-hip ratio and total cardiovascular risk factors. Additional parameters measuring extent of obesity are percentage body fat and total body fat. Subjects suffering from obesity have a BMI value of above 25. In some embodiments the term "obesity" includes subjects having BMI values of between about 25.0 to about 29.9 (overweight), in some further embodiments between about 30.0 to about 34.9 (class I obesity), in yet further embodiments between about 35.0 to about 39.9 (class II obesity), in further embodiments above 40.0 (class III obesity), in other embodiments between about 40 to about 49.9 (morbid obesity) and in other embodiments ≥50 (super obesity).

In another one of its aspects the invention provides a method of treatment or prevention of at least one condition selected from hyperglycemia, diabetes, altered insulin secretion, insulin resistance, cardiovascular disorder, obesity and metabolic syndrome X; said method comprising administering to a subject in need thereof an effective amount of a compound of general formula (I), formula (II) or formula (III), as defined herein above.

The term "treatment" as used herein refers to the administering of a therapeutic amount of a compound and/or a composition of the present invention which is effective to ameliorate undesired symptoms associated with a disease, to prevent the manifestation of such symptoms before they occur, to slow down the progression of the disease or condition, slow down the deterioration of symptoms, to enhance the onset of remission period, slow down the irreversible damage caused in the progressive chronic stage of the disease or condition, to delay the onset of said progressive stage, to lessen the severity or cure the disease or condition, to improve survival rate or more rapid recovery, or to prevent the disease or condition form occurring or a combination of two or more of the above.

The "effective amount" for purposes disclosed herein is determined by such considerations as may be known in the art. The amount must be effective to achieve the desired therapeutic effect as described above, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half life in the body, on undesired side effects, if any, on factors such as age and gender, etc.

According with another aspect, the present invention provides a compound having the general formula (I), for use in treating or preventing at least one condition selected from hyperglycemia, diabetes, altered insulin secretion, insulin resistance, cardiovascular disorder, obesity and metabolic syndrome X:

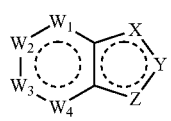

wherein

X, Y, Z are each independently selected from the group consisting of N, S, O, CH, C—SH, C—NH, —C—OH, —N—SH, NH, N-linker-$R_1$, C-linker-$R_1$;

$W_1$, $W_2$, $W_3$, $W_4$ are each independently selected from the group consisting of N, $CR_2$;

linker is independently selected from the group consisting of —S—, —S—S—, —S—$(CH_2)_n$—, —NH—, —NH—$(CH_2)_n$—, —O—, —$SO_2$—, arylene, heteroarylene;

n is 1 to 5;

$R_1$ is selected from the group consisting of straight or branched $C_4$-$C_{20}$ alkyl, straight or branched $C_4$-$C_{20}$ alkenyl, straight or branched $C_4$-$C_{20}$ alkynyl, each optionally interrupted with at least one NH, $C_5$-$C_7$ saturated cycloalkyl or heteroalkyl ring, $C_5$-$C_{12}$ aromatic or heteroaromatic ring, each optionally substituted with at least one group selected from —COOH, —$NH_2$, $C_1$-$C_8$ alkoxy, $C_1$-$C_5$ amidyle, $C_1$-$C_5$ carboxyl, halogen;

$R_2$ is independently selected from the group consisting of H, OH, SH, $NH_2$, $NO_2$, halogen, CN, $C_1$-$C_8$ alkoxy, $C_1$-$C_5$ carboxylic acid, straight or branched $C_1$-$C_8$ alkyl, straight or branched $C_2$-$C_{10}$ alkenyl, straight or branched $C_2$-$C_{12}$ alkynyl each optionally substituted by at least one substituent selected from the group consisting of $C_1$-$C_5$ alkoxy, $C_1$-$C_5$ carboxylic acid, OH, SH, $NH_2$, halogen.

According with another aspect, the present invention provides a compound of general formula (IV), for use in the treatment or prevention of at least one condition selected from hyperglycemia, diabetes, altered insulin secretion, insulin resistance, cardiovascular disorder, obesity and metabolic syndrome X:

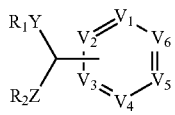

wherein $V_1$, $V_2$, $V_3$, $V_4$, $V_5$ and $V_6$ are each independently selected from N, C, CH and $CR_3$;

Y and Z are each independently S or O;

$R_1$ and $R_2$ are each independently selected from straight or branched $C_1$-$C_{20}$ alkyl, straight or branched $C_2$-$C_{20}$ alkenyl, straight or branched $C_2$-$C_{20}$ alkynyl, each optionally interrupted with at least one NH; or wherein $R_1$ and $R_2$ together with Y, Z and the carbon atom connecting them a 5 to 10 membered ring; optionally substituted by at least one group selected from straight or branched $C_1$-$C_{10}$ alkyl, straight or branched $C_2$-$C_{10}$ alkenyl, straight or branched $C_2$-$C_{10}$ alkynyl;

$R_3$ is selected from the group consisting of halogen, straight or branched $C_1$-$C_{20}$ alkyl, straight or branched $C_2$-$C_{20}$ alkenyl, straight or branched $C_2$-$C_{20}$ alkynyl; amidyle carboxy, $SO_2$, cabamate, optionally substituted by 1,3-dithian-benzyl It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any integer or step or group of integers and steps.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1 shows that compounds 3, 4 and 15 increase the rate of glucose uptake in L6 myotubes by activating AMPK.

FIG. 3 shows the effect of compound 34 on GLUT-4 translocation to the plasma membrane of L6 myotubes.

FIG. 4 shows the antihyperglycemic effects of 34 in diabetic KKAy mice.

DETAILED DESCRIPTION OF EMBODIMENTS

Materials

Figure 1A:
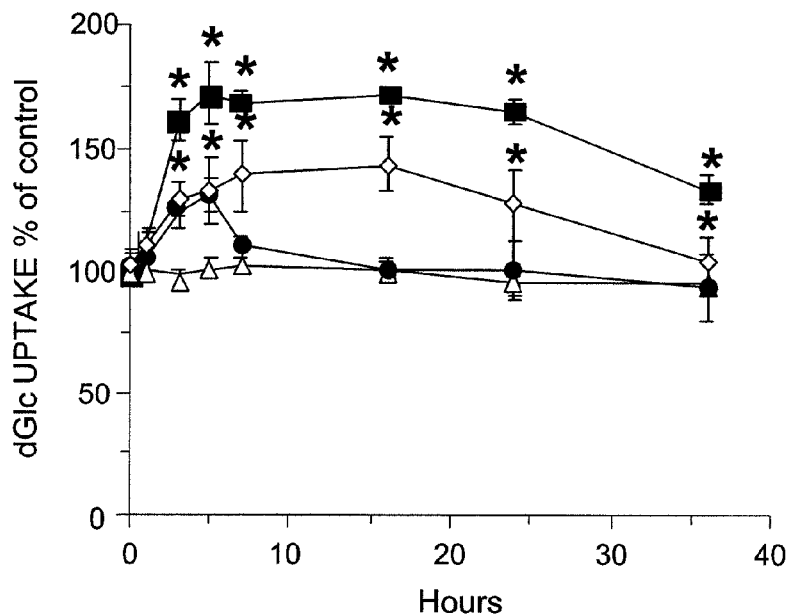
FIG. 1A shows a time-course analysis of dGlc uptake in myotube cultures that were washed and incubated in αMEM supplemented with 2% (v/v) FCS, 23.0 mM D-glucose and 100 μM of 3 (●), 4 (■) or 15 (◇); DMSO (Δ).
Figure 1B:
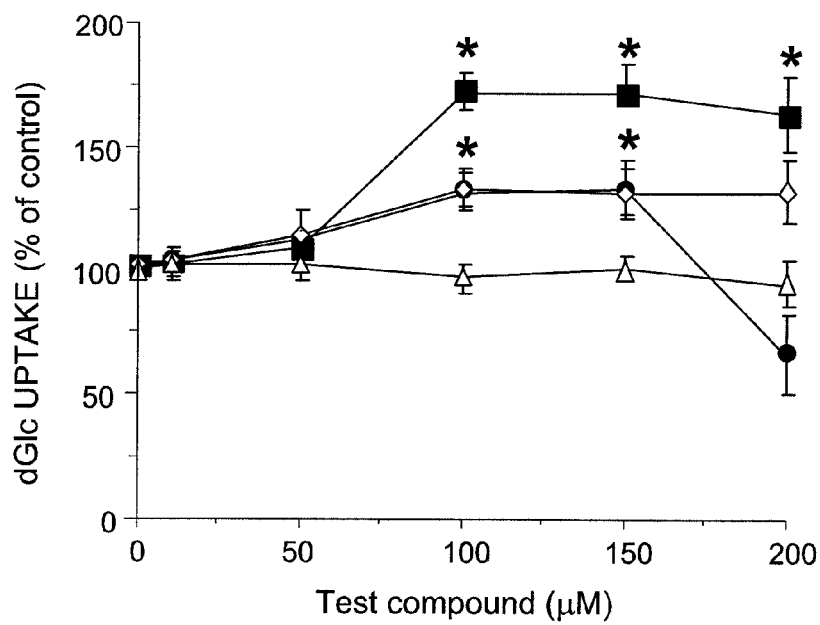
FIG. 1B shows a dose response analysis of myotube cultures incubated for the indicated time, with the indicated concentrations of 3 (●, 5 h), 4 (■, 12 h) or 15 (◇, 12 h).
Figure 1C:
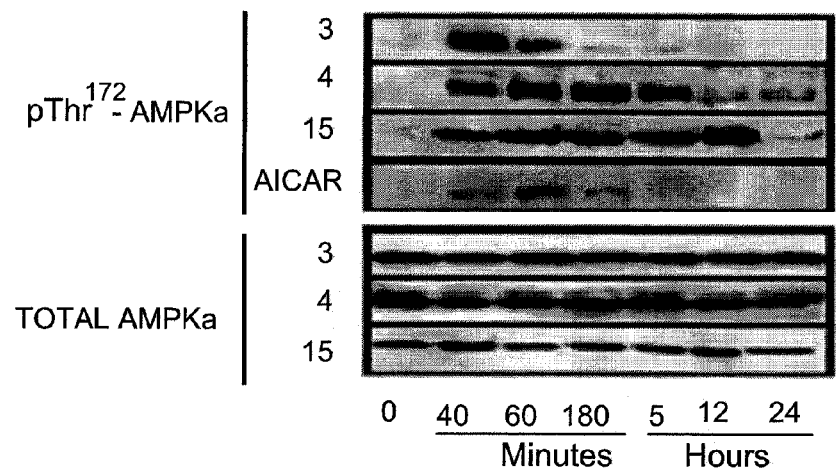
FIG. 1C shows AMPK activation: L6 myotube cultures treated with 100 μM of 3, 4, 15, or 4 mM AICAR for the indicated times. Representative blots are shown.
Figure 1D:
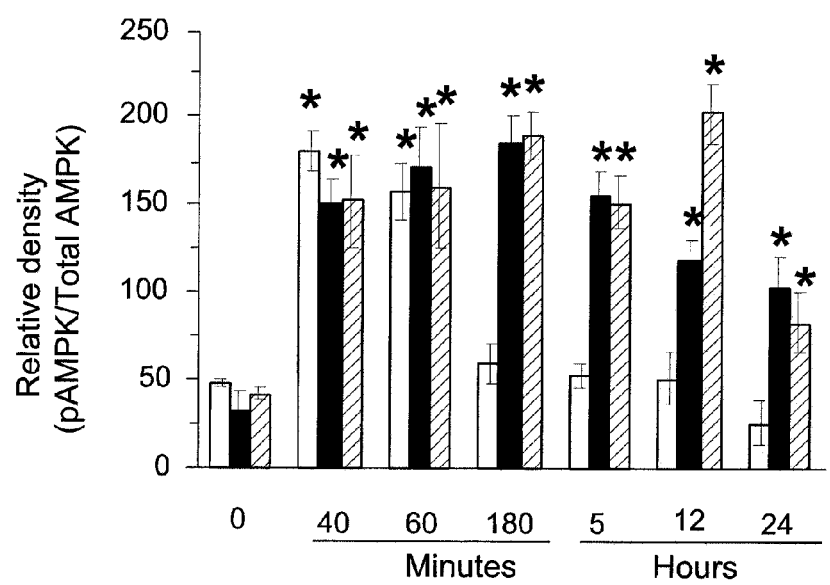
FIG. 1D shows the band density measurements of three independent experiments of Compound 3 (open bars), 4 (black bars) and 15 (hatched bars). *$p<0.05$, in comparison to the respective controls.

Human insulin (Actrapid) was purchased from Novo Nordisk (Bagsvaerd, Denmark). AICAR, BSA (bovine serum albumin, fraction V), 6-ethoxybenzothiazole-2-thiol (4), dGlc, D-glucose, OPD, and the protease inhibitor cocktail were purchased from Sigma-Aldrich Chemicals (Rehovot, Israel). (E)-2-Amino-5-((E)-3-(5-nitrofuran-2-yl)allylidene)thiazol-4(5H)-one (2) was from Synthon-Lab Ltd. (St. Petersburg, Russia). Chemical Block Ltd. (Moscow, Russia) supplied 2-amino-5-ethylthiazol-4(5H)-one (3). Glycerol and sodium fluoride were from Merck (Whitehouse Station, N.J., USA). Mercaptoethanol, PMSF, sodium orthovanadate, sodium-β-glycerophosphate, sodium pyrophosphate and sodium dodecyl sulfate (SDS) were purchased from Alfa Aesar (Ward Hill, Mass.). American Radiolabeled Chemicals (St. Louis, Mo.) supplied [$^3$H]dGlc [2.22 TBq/mmol (60 Ci/mmol)] and [$^{14}$C—(U)]sucrose (22.2 GBq/mmol). Antibodies against AMPK and pThr$^{172}$ AMPK were purchased from Cell Signaling Technology (Beverly, Md.). Anti-C-Myc (A-14) antibody was from Santa Cruz Biotechnology (Santa Cruz, Calif.), horseradish peroxidase-conjugated anti-rabbit IgG and EZ-ECL chemoluminescence detection kit were from Jackson ImmunoResearch (West Grove, Pa.). Goat serum, fetal calf serum (FCS), L-glutamine, α-MEM and antibiotics were purchased from Biological Industries (Beth-Haemek, Israel). Organic solvents (HPLC grade) were from Frutarom Ltd. (Haifa, Israel). Dry THF was obtained using distillation from a boiled blue color mix with sodium/benzophenone. The melting points were determined with Fisher-Johns melting point apparatus (Palmerton, Pa.). The $^1$H NMR and $^{13}$C NMR spectra were recorded at room temperature on a Bruker Advance NMR spectrometer (Vernon Hills, Ill.) operating at 200 and 300 MHz and were in accord with the assigned structures. Chemical shift values were reported relative to tetramethylsilane (TMS) that was used as an internal standard. The samples were prepared by dissolving the synthesized compounds in DMSO-d$_6$ ($\delta_H$=2.50 ppm, $\delta_C$=39.52 ppm) or in CDCl$_3$ ($\delta_H$=7.26 ppm, $\delta_C$=77.16 ppm) [20]. Chemical shifts were expressed in δ (ppm) and coupling constants (J) in hertz. The splitting pattern abbreviations are as follows: s, singlet; d, doublet; t, triplet; q, quartet; qui, quintet; seq, sextet; m, unresolved multiplet due to the field strength of the instrument; dd, doublet of doublet.

A QT of micro spectrometer (Micromass, Milford, Mass.) in the positive ion mode was used for mass spectrometry. Data were processed using massLynX v.4.1 Calculation and deconvolution software (Waters Corporation, Milford, Mass.). Column chromatography was performed on Merck Silica gel 60 (230-400 mesh; Merck, Darmstadt, Germany). Analytical and preparative HPLC (Young Lin Instruments, Anyang, Korea) were performed on LUNA C18 preparative (10 μm, 100×30 mm) or analytical (5 μm, 250×4.6 mm) columns, both from Phenomenex Inc. (Torrance, Calif.). Acetonitrile and doubly distilled water were used as an eluent in different ratios. Analytical thin layer chromatography was carried out on pre-coated Merck Silica gel 60F$_{254}$ (Merck) sheets using UV absorption and iodine physical adsorption for visualization.

Example 1

Synthesis of Compounds

Compounds of the invention may be synthesized according to the schemes and methods described below. The reagents and conditions described are intended to be exemplary and not limiting. As one of skill in the art would appreciate, various analogs may be prepared by modifying the synthetic reactions such as using different starting materials, different reagents, and different reaction conditions (e.g., temperature, solvent, concentration, etc.)

The synthesis of 19 as shown below was performed using AlCl$_3$ catalysis for de-etherification of the phenol ethoxyether moiety from 4, as described by Woltersdorf et al (*J Med Chem*, 32 (1989) 2486-2492).

Compounds 20-29 were readily produced by the reaction of free phenol or free thiol groups in 4 with the respective alkylalide, in the presence of sodium hydride in dry THF, as shown in below. Sulfanilamide 30 was produced in a two-step synthetic procedure, as described by Woltersdorf et al. Compounds 31 and 32 were obtained using a novel synthetic approach that we developed by employing reflex in concentrated HCl overnight to form an S—S bond. In addition, the amide derivative 33 was obtained in a two-step procedure: first, the carboxylic acid derivative of 4 was synthesized (24) followed by coupling of a propyl amine to 24, using the coupling reagent 1-ethyl-3-(3-dimethyllaminopropyl)carbodiimide hydrochloride (EDC)/hydroxybenzotriazole (HOBt). The lead compound (34) was prepared by forming a thioether bond between 4 and the chlorinated intermediate, 2-(chloromethyl)benzothiazole. This benzothiazole derivative was synthesized from 2-methylbenzothiazole, using 3-chloroisocyanuric acid as a chlorinating agent. All compounds were analyzed by analytical HPLC followed by gravitational column chromatography, or by preparative HPLC. The purified compounds were characterized by melting point, $^1$HNMR, $^{13}$CNMR and MS analyses.

In one aspect, the present invention provides methods for the synthesis of compounds of formula I and intermediates thereto. In some embodiments, such methods are as shown in Scheme 1 and Scheme 2 and details provided below.

Scheme 1

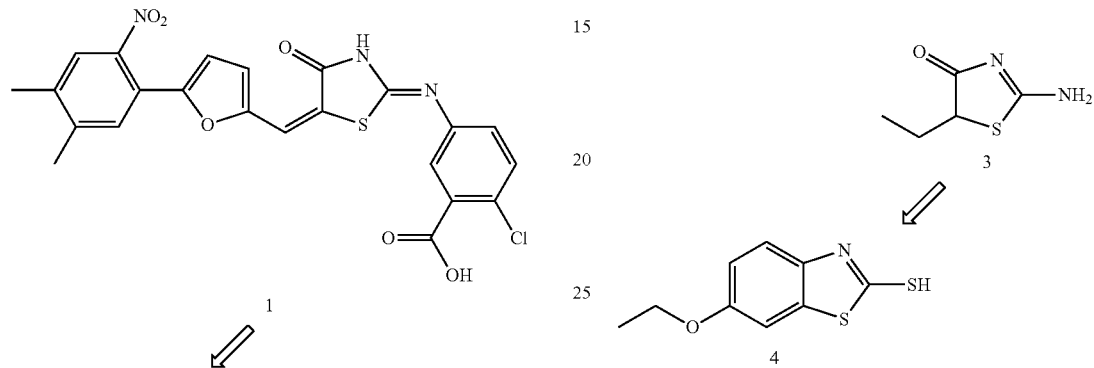

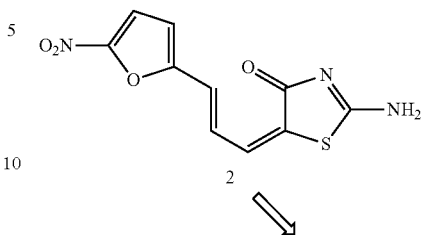

Scheme 2

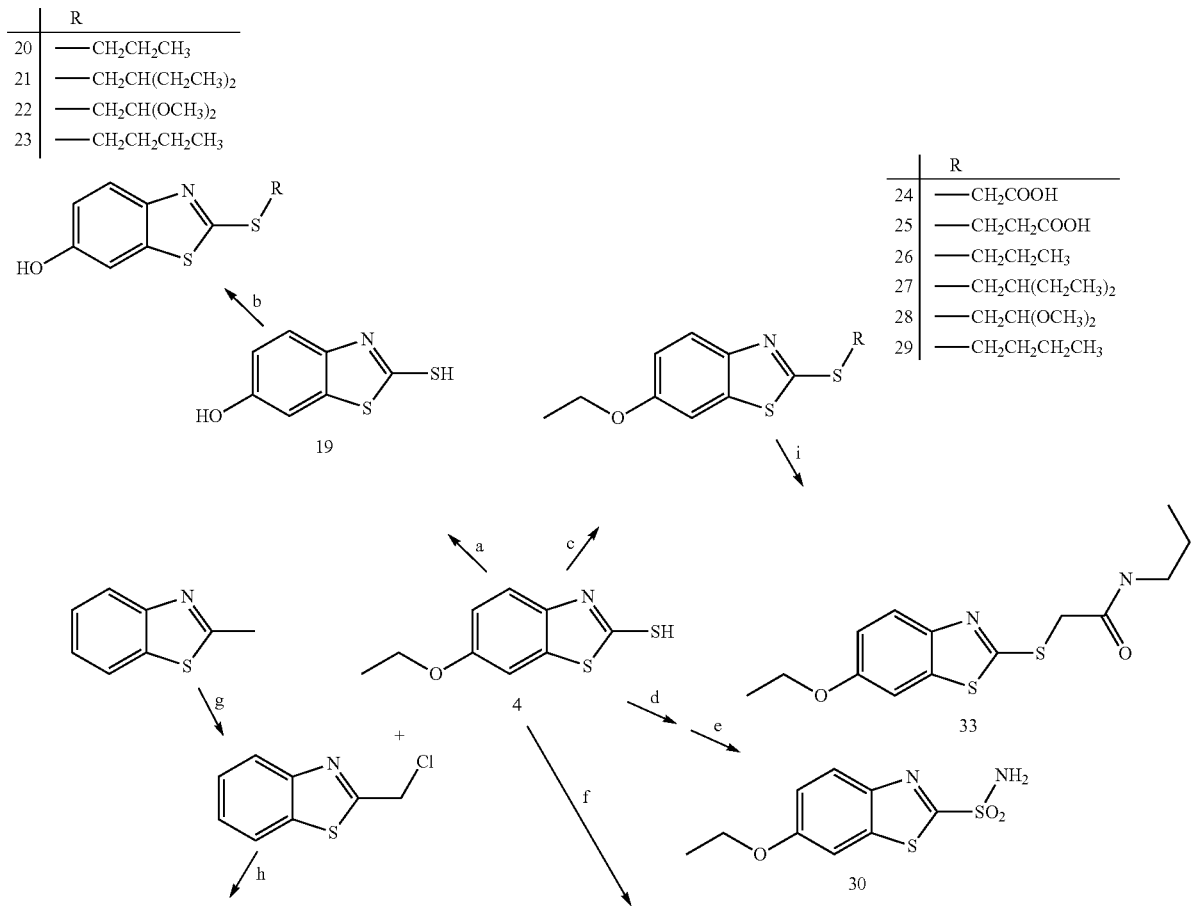

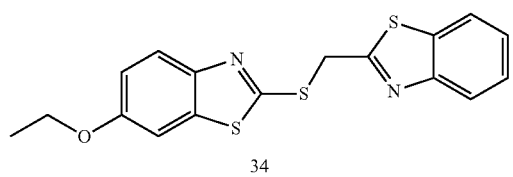

34

-continued

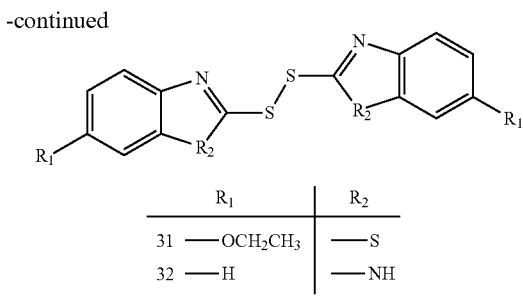

| | $R_1$ | $R_2$ |
|---|---|---|
| 31 | —OCH$_2$CH$_3$ | —S |
| 32 | —H | —NH | wherein (a) AlCl$_3$, (CH$_2$Cl$_2$)$_2$; (b) NaH, dry THF, alkyl halide; (c) NaH, dry THF, chloropropionic or chloroacetic acid or alkyl halide; (d) NH$_4$OH$_{(aq)}$, NaOCl$_{(aq)}$; (e) KMnO$_4$, H$_2$O, Me$_2$CO; (f) HCl conc., THF, reflux, overnight; (g) trichloroisocyanuric acid, CHCl$_3$, reflux, overnight; (h) diisopropylethylamine, DMAP, THF, reflux, overnight; (i) EDC/HOBt.

General Procedure for the Synthesis of S-Alkyl Benzothiazoles (20-23).

To an ice-cold stirred solution of 2-mercaptobenzothiazol-6-ol (19) (0.2 g, 1.09 mmol) in dry THF (15 ml) sodium hydride (0.11 g, 4.58 mmol) was added in three portions. Then, the appropriate alkylhalide (2.73 mmol in dry THF, 2 ml) was added drop-wise to the reaction solution. Stirring at 0° C. was continued for 1 hour followed by additional 1 hour incubation at room temperature. The reaction progress was followed by TLC (100% CH$_2$Cl$_2$). The reaction was quenched by the addition of ice (about 15 g) followed by 100 ml of chloroform. The organic layer was separated, washed twice in water, dried over sodium sulfate, filtered and evaporated to yield the solid product. The compounds were purified by column chromatography using 100% dichloromethane as an eluent.

2-(propylthio)benzothiazol-6-ol (20)

Yield 25%. Yellow crystalline mass, m.p. 67-70° C. $^1$H NMR (CDCl$_3$): δ 1.05-1.10 (t, 3H, J=7.0), 1.81-1.88 (m, 2H), 3.26-3.30 (t, 2H, J=7.2), 6.89-6.93 (dd, 1H, J=2.5, 6.3), 7.19-7.20 (d, 1H, J=2.7), 7.70-7.73 (d, 1H, J=8.7). $^{13}$C NMR (CDCl$_3$): δ 13.2, 22.6, 35.8, 101.7, 106.7, 115.4, 121.7, 139.5, 147.1, 153.5. MS: MW=225.33 g/mol, MH$^+$=226.

2-(2-ethylbutylthio)benzothiazol-6-ol (21)

Yield 50%. White powder, m.p. 105-110° C. $^1$H NMR (CDCl$_3$): δ 0.86-0.93 (t, 3H, J=9.0), 1.43-1.52 (qui, 4H, J=4.8), 1.65-1.70 (m, 1H), 3.32-3.34 (d, 2H, J=6.3), 6.90-6.93 (dd, 1H, J=2.5, 6.3), 7.20-7.21 (d, 1H, J=2.4), 7.69-7.72 (d, 1H, J=8.7). $^{13}$C NMR (CDCl$_3$): δ 10.7, 25.1, 40.5, 44.5, 106.8, 115.2, 121.9, 130.9, 150.8, 166.4, 168.5. MS: MW=267.41 g/mol, MH$^+$=268.

2-(2,2-dimethoxyethylthio)benzothiazol-6-ol (22)

Yield 62% Yellow solid.
$^1$H NMR (CDCl$_3$): δ 3.43 (s, 6H), 3.52 (d, 2H, J=5.4), 4.68 (t, 1H, J=5.4), 6.90-6.94 (dd, 1H, J=2.5, 6.3), 7.2 (d, 1H, J=2.4), 7.32 (d, 1H, J=8.7). $^{13}$C NMR (CDCl$_3$): δ 31.9, 58.3, 106.0, 114.5, 121.2, 137.3, 143.0, 151.8, 168.5.

2-(butylthio)benzothiazol-6-ol (23)

Yield 60%. Light brown crystals, m.p. 80-85° C. $^1$H NMR (CDCl$_3$): δ 0.93-0.98 (t, 3H, J=7.3), 1.43-1.55 (seq, 2H, J=7.4), 1.74-1.83 (qui, 2H, J=7.3), 3.28-3.33 (t, 2H, J=7.3), 6.90-6.94 (dd, 1H, J=2.5, 6.3), 7.20-7.21 (d, 1H, J=2.4), 7.69-7.72 (d, 1H, J=8.7). $^{13}$C NMR (CDCl$_3$): δ 13.6, 21.9, 31.3, 33.7, 106.7, 115.3, 121.9, 133.9, 147.7, 153.2, 165.5. MS: MS=239.36 g/mol, MH$^+$=240.

General Procedure for the Synthesis of Benzothiazole Carboxylic Acid Derivatives (24-25).

To an ice-cold stirred solution of 4 (1 g, 4.73 mmol) in dry THF (25 ml) sodium hydride (14.19 mmol, 0.34 g) was added in three portions. Then, chloroacetic acid (0.77 g, 7.1 mmol) or chloropropionic acid (0.67 g, 7.1 mmol) were added dropwise. Stirring at 0° C. was continued for additional 1 hour at room temperature. The reaction was quenched by the addition of ice (about 15 g) and 10 ml of 0.1 M cold hydrochloric acid. Chloroform (100 ml) was added and the organic layer was separated, washed twice with water, dried over sodium sulfate, filtered and evaporated to give the product.

2-(6-ethoxybenzothiazol-2-ylthio)acetic acid (24)

The compound was purified by crystallization from THF/Methanol/Dichloromethane (1:1:1). Yield 10%. Brown solid, m.p. 125-130° C. $^1$H NMR (DMSO-d$_6$): δ 1.41-1.48 (t, 3H, J=6.9), 4.11-4.22 (q, 2H, J=6.9), 4.30 (s, 2H), 7.10-7.16 (dd, 1H, J=2.5, 6.4), 7.69-7.70 (d, 1H, J=2.4), 7.79-7.84 (d, 1H, J=9). $^{13}$C NMR (DMSO-d$_6$): δ 14.9, 35.3, 63.9, 105.8, 115.7, 121.9, 136.4, 156.2, 163.5, 169.6, 210.5. MS: MW=269.34 g/mol, MH$^+$=270.

3-(6-ethoxybenzothiazol-2-ylthio)propanoic acid (25)

The compound was purified as described for 24. Yield 30%. Brown crystals, m.p. 175-178° C. $^1$H NMR (DMSO-d$_6$): δ 1.30-1.34 (t, 3H, J=6.9), 2.70-2.74 (t, 2H, J=6.3), 3.74-3.78 (t, 2H, J=6.3), 3.98-4.05 (q, 2H, J=6.9), 6.95-6.99 (dd, 1H, J=2.5, 6.3), 7.18-7.23 (d, 1H, J=9.0), 7.31-7.32 (d, 1H, J=2.4). $^{13}$C NMR (DMSO-d$_6$): δ 14.9, 28.48, 34.1, 64.0, 106.7, 113.3, 115.4, 121.9, 135.4, 140.1, 158.9, 172.1. MS: MW=283.37 g/mol, MH$^+$=284.

General Procedure for the Synthesis of S-alkyl 6-ethoxybenzothiazoles (26-29).

These compounds were synthesized according to the synthetic procedure for S-alkyl benzothiazoles, using was 6-ethoxy-2-mercaptobenzothiazol as the starting molecule (4).

6-ethoxy-2-(propylthio)benzothiazole (26)

The remaining yellow syrup was further purified by silica gel column chromatography (Eluent: 100% Dichloromethane). Attempts to crystallize the syrup were unsuccessful. Yield 10%. Colorless syrup. $^1$H NMR (CDCl$_3$): δ

1.05-1.13 (t, 3H, J=7.4), 1.37-1.44 (t, 2H, J=7), 1.73-1.91 (seq, 2H, J=7.3), 3.23-3.30 (t, 2H, J=7.2), 3.96-4.07 (q, 2H, J=6.9), 6.94-7.0 (dd, 1H, J=2.5, 6.3), 7.17-7.18 (d, 1H, J=2.4), 7.70-7.75 (d, 1H, J=9). $^{13}$C NMR (CDCl$_3$): δ 13.2, 14.7, 22.6, 35.5, 63.9, 104.6, 115.0, 121.7, 136.3, 147.7, 156.2, 163.7. MS: MW=253.38 g/mol, MH$^+$=254.

6-ethoxy-2-((2-ethylbutyl)thio)benzothiazole (27)

The compound was obtained as a yellow syrup that was further purified by silica gel column chromatography (Eluent: 100% Dichloromethane). Attempts to crystallize the syrup were unsuccessful. Yield 10%. Colorless syrup. $^1$H NMR (CDCl$_3$): δ 0.91-0.95 (t, 6H, J=7.3), 1.41-1.50 (qui, 3H, J=7), 1.63-1.7 (m, 1H), 3.32-3.34 (d, 2H, J=6.3), 4.01-4.08 (q, 2H, J=7), 6.97-7.0 (dd, 1H, J=2.5, 6.3), 7.20-7.21 (d, 1H, J=2.4), 7.71-7.74 (d, 1H, J=9). $^{13}$C NMR (CDCl$_3$): δ 10.9, 14.9, 25.2, 37.6, 40.7, 64.1, 104.8, 115.1, 121.8, 136.4, 147.8, 156.3, 165.3, 175.8. MS: MW=295.46 g/mol, MH$^+$=296.

2-((2,2-dimethoxyethyl)thio)-6-ethoxybenzothiazole (28)

Yield 15%. Colorless syrup. $^1$H NMR (CDCl$_3$): δ 1.40 (t, 3H, J=7), 3.45 (d, 2H, J=4.6), 4.68 (q, 2H, J=7), 4.17 (s, 6H), 6.92 (dd, 1H, J=2.5, 6.3), 7.13 (d, 1H, J=2.4), 7.56 (d, 1H, J=8.7). $^{13}$C NMR (CDCl$_3$): δ 14.1, 31.9, 58.3, 64.1, 106.0, 114.5, 114.3, 121.2, 137.3, 143.0, 151.8, 168.5.

2-(butylthio)-6-ethoxybenzothiazole (29)

The compound was purified by silica gel column chromatography (Eluent: 100% Dichloromethane). Yield 30%. Colorless crystalline needles. m.p. 30-35° C. $^1$H NMR (CDCl$_3$): δ 1.08-1.15 (t, 3H, J=7), 1.56-1.74 (m, 5H), 1.87-2.02 (qui, 2H, J=5.6), 3.42-3.50 (t, 2H, J=7.3), 4.16-4.26 (q, 2H, J=7), 7.12-7.18 (dd, 1H, J=2.5, 6.3), 7.36-7.37 (d, 1H, J=2.4), 7.88-7.92 (d, 1H, J=9). $^{13}$C NMR (CDCl$_3$): δ 13.5, 14.7, 21.8, 31.2, 33.4, 63.9, 104.6, 115.0, 212.8, 136.3, 147.7, 156.2, 163.8. MS: MW=267.41 g/mol, MH$^+$=268.

General Procedure for the Synthesis of Disulfides 31 and 32

Compound 4 (1 g, 4.7 mmol) or 2-mercaptobenzimidazole (1 g, 6.7 mmol) was dissolved in 15 ml of THF. Concentrated HCl (0.15 ml, 4.7 mmol or 0.21 ml, 6.7 mmol, respectively) was added to the reaction mixture under intensive stirring. The reaction was refluxed overnight then cooled to room temperature, and 100 ml of chloroform (100 ml) were added followed by the addition of 15 ml of saturated sodium bicarbonate solution. The organic phase was separated, washed twice by water, dried over sodium sulfate, filtered and the crystalline product was separated.

1,2-bis(6-ethoxybenzothiazol-2-yl)disulfane (31)

Yield 10%. White crystals, m.p. 185-190° C. $^1$H NMR (DMSO-d$_6$): δ 1.39-1.43 (t, 6H, J=7.0), 3.99-4.06 (q, 4H, J=7.0), 6.86-6.90 (dd, 2H, J=2.5, 6.4), 6.96-6.97 (d, 2H, J=2.4), 7.20-7.23 (d, 2H, J=8.8). $^{13}$C NMR (DMSO-d$_6$): δ 14.8, 64.0, 106.7, 113.3, 115.4, 131.0, 135.4, 156.1, 186.2. MS: MW=420.59 g/mol, MH$^+$=421.

1,2-di(1H-benziimidazol-2-yl)disulfane (32)

Yield 10%. Yellow crystals, m.p. 195-200° C. $^1$H NMR (DMSO-d$_6$): δ 7.12 (s, 8H), 12.53 (s, 2H). $^{13}$C NMR (DMSO-d$_6$): δ 109.7, 122.6, 132.5, 168.4. MS: MW=298.39 g/mol, MH$^+$=299.2

Synthesis of 2-((6-ethoxybenzothiazol-2-yl)thio)-N-propylacetamide (33)

To a stirred solution of 24 (110.3 mg, 0.41 mmol) and n-propylamine (50.5 mg, 0.50 mmol) in CHCl$_3$ (2.0 ml), HOBt (190 mg, 1.41 mmol) and EDC (120 mg, 0.63 mmol) were added at room temperature. After stirring for 20 hours, the reaction mixture was diluted with EtOAc, washed with saturated NaHCO$_3$ solution and brine, dried (MgSO$_4$), and concentrated in vacuo. The residue was purified by HPLC (gradient from 20%, acetonitrile 80% in DDW to 100% acetonitrile, in 15 minutes) to give 33 (57.9 mg, 36% yield) as a brown amorphous solid, range of m.p. temperature was too large for a clear determination. $^1$H NMR (DMSO-d$_6$): δ 0.97 (t, 3H, J=6.8), δ 1.27 (t, 3H, J=7.1), δ 1.53 (m, 2H, J=6.8, 3.5), δ 3.54 (d, 2H, J=3.7), δ 4.01 (s, 2H), δ 4.19 (q, 2H, J=7.3), δ 6.23 (amide broad peak), δ 6.97 (dd, 1H, J=10.8, J=3.7), 7.33 (d, 2H, J=8.8). $^{13}$C NMR (DMSO-d$_6$): δ 12.8, 13.76, 20.6, 39.56, 40.78, 65.1, 101.79, 114.78, 123.6, 135.79, 145.8, 154.67, 168.4, 169.95. MS: MW=310.07 g/mol, MNa$^+$=333.18 g/mol.

Synthesis of 2-((benzothiazol-2-ylmethyl)thio)-6-ethoxybenzothiazole (34)

The compound 2-(chloromethyl)benzothiazole [15] (1 g, 5.45 mmol), dissolved in THF (50 ml), was added drop-wise to a stirred solution of 4 (1.15 g, 5.45 mmol), N-ethyldiisopropylethylamine (1.35 ml, 8.17 mmol) and 4-dimethylaminopyridine (0.08 g, 0.545 mmol) in THF (50 ml). The reaction mixture was refluxed overnight. Then, the solution was cooled to room temperature, and water (100 ml) followed by chloroform (100 ml) were added. The organic layer was separated, washed twice in water, dried over sodium sulfate, filtered and evaporated. The crude solid was purified by column chromatography using 100% dichloromethane as an eluting solvent. The compound was obtained as dark brown solid. Yield 35%, m.p. 78-82° C. $^1$H NMR (DMSO-d$_6$): δ 1.31-1.33 (t, 3H, J=3.45), 4.02-4.08 (q, 2H, J=6.9), 5.08 (s, 2H), 7.02-7.06 (dd, 1H, J=2.5, 6.3), 7.42-7.50 (m, 2H), 7.59-7.60 (d, 1H, J=2.4), 7.74-7.77 (d, 1H, J=9.0), 7.95-8.06 (dd, 2H, J=8.1, 15.3). $^{13}$C NMR (DMSO-d$_6$): δ 14.8, 35.1, 64.1, 104.8, 115.6, 121.6, 122.3, 125.3, 126.2, 141.9, 143.1, 152.6, 165.6, 173.0, 178.4. MS: MW=358.50 g/mol, MH$^+$=359.

Example 2

In Vitro Studies

The effect of the various derivatives on the rate of glucose uptake in L6 myotubes was investigated. Several in vitro screening systems were used: first, the rate of glucose uptake in L6 myotubes was assessed by measuring the uptake of the non-metabolizable tritiated glucose analog 2-[$^3$H,1-]deoxy-D-glucose (dGlc). Second, the extent of Thr$^{172}$ phosphorylation of AMPK in treated L6 myotubes was determined by Western blot analysis in whole cell lysates. The abundance of GLUT1 and GLUT4 in the plasma membranes of L6 myotubes was determined in cells expressing GLUT-1myc or GLUT-4myc, as described before. In addition, to evaluate if the active derivatives increase the rate of glucose transport in a non-insulin dependent manner, two inhibitors of the insulin transduction pathway were used: the phophoinositol-3-kinase (PI3K) inhibitor wortmannin and the AKT inhibitor 1,3-dihydro-1-(1-((4-(6-phenyl-1H-imidazo[4,5-g]quinoxalin-7-yl)phenyl)methyl)-4-piperidinyl)-2H-benzimidazol-2- one-tri-fluoroacetate salt hydrate [16]. In addition, the effect of compounds on the glucose—stimulated insulin secretion (GSIS) was investigated.

L6 Myotube Cultures

L6 myotubes were maintained as described in [21]. All experiments were conducted on fully differentiated myotubes.

INS-1E Cell Cultures

INS-1E cells (passages 70-90) were grown and maintained as described in Merglen A et al. Endocrinology 2004, 145: 667-678.

2-[$^3$H,1]-Deoxy-D-glucose Uptake Assay

The rate of [$^3$H]dGlc uptake in myotubes, in the absence or presence of insulin, was determined as described in [21]. Briefly, L6 myotube cultures were preincubated in α-MEM supplemented with 2% (v/v) FCS and 23.0 mM D-glucose for 24 hours, and then treated as described in the Figures. The insulin effect was measured after its addition (200 nM) to cultures for the last 30 minutes of treatment. The cultures were then rinsed 3 times with PBS at room temperature and incubated with PBS, pH 7.4, containing 0.1 mM dGlc and 1.0 µCi/ml [$^3$H]dGlc for 5 minutes at room temperature. At the end of the assay, the myotubes were lysed in 0.1% (w/v) SDS in water and taken for liquid scintillation.

Preparation of Cell Lysates and Western Blot Analysis

Whole cell lysates were prepared as previously described [21] with some minor modifications: the lysis buffer contained 50 mM Tris-HCl, pH 7.5, 1 mM EDTA, 1 mM EGTA, 1 mM Na$_3$VO$_4$, 150 mM NaCl, 50 mM NaF, 10 mM sodium-glycerophosphate, 5 mM sodium pyrophosphate, and 1 mM PMSF, supplemented with 0.1% (v/v) NP-40, 0.1% (v/v) 2-β-mercaptoethanol, and protease inhibitor cocktail (1:100 dilution). The cells were washed by ice-cold PBS, and 1 ml of lysis buffer was then added and incubated at 4° C. for 40 minutes. The resulting cell lysates were centrifuged at 8,700 g×30 minutes at 4° C. and the resulting supernatant fractions were separated and kept at −20° C. until used. Protein content in the supernatant was determined according to Bradford, using a BSA standard dissolved in the same buffer. Aliquots (5-60 µg of protein) were mixed with the sample buffer [62.5 mM Tris-HCl, pH 6.8, 2% (w/v) SDS, 10% (v/v) glycerol, 50 mM DTT, and 0.01% (w/v) bromophenol blue], heated at 95° C. for 5 minutes. Samples for Western blot analyses of GLUT1 and GLUT4 were prepared as described in [22]. The proteins were separated on 10% SDS-PAGE and Western blot analyses performed using antibodies according to our previously established protocols.

Colorimetric Determination of Surface GLUT1myc and GLUT4myc in L6 Myotubes

The colorimetric detection of surface GLUT4myc or GLUT1myc in L6 myotubes was performed as described in [7]. Briefly, cultured myotubes were incubated with rabbit anti-C-Myc antibody (1:200 dilution), washed and fixed with 3% formaldehyde, and further interacted with goat HRP-conjugated anti-rabbit IgG (1:2000 dilution). Following the washes, a solution of OPD was added, and the culture plates were taken for absorbance measurement at 492 nM to estimate the relative abundance of GLUT1myc or GLUT4myc on the plasma membrane of the myotubes. The GLUT1myc and GLUT4myc L6 cell cultures were the courtesy of Dr. A. Klip, Hospital for Sick Children (Toronto, ON, Canada).

Glucose-Stimulated Insulin Secretion (GSIS) and Insulin Radioimmunoassay

To investigate the glucose—stimulated insulin secretion (GSIS) and insulin radioimmunoassay-confluent cultures of INS-1E cells were pre-incubated for 30 min in KRBH-BSA buffer containing 3.3 mM glucose. This was followed by 1-h incubation at 3.3 and an additional 1-h at 16.7 mM glucose, as described (1). Aliquots from the incubation buffers were collected, cleared by centrifugation and frozen until used for insulin RIA. Total insulin content in β-cells was similarly measured in aliquots of cell extracts (1). RIA kits rat insulin (Linco Research, St. Charles, Mo.) was used according to manufacturers' protocols.

Example 3

In Vivo Experiments

The effect of the various ethoxybenzo-thiazol derivatives on the blood glucose level in diabetic KKAy mice was investigated. The in vivo antihyperglycemic effect of the lead compound was investigated in hyperglycemic and hyperinsulinemic KKAy mice, an established animal model for T2DM, after subcutaneous injections. Venous blood samples from small tail clips were taken for glucose determination. Finally, to investigate the effect of the lead compound on whole body glucose disposal in the mice we performed standard IP-GTT tests following an overnight fast.

Diabetic male KKAy mice (8 to 12-week old, 20-25 g) were purchased from The Jackson Laboratory (Bar Harbor, Me.). The animals were routinely kept in 12-h light/dark cycles and provided with food and water ad libitum. Blood glucose levels at sacrifice ranged between 17-25 mmol/l. The ethics committee (IACUC) of the Hebrew University of Jerusalem approved the study protocol for animal welfare. The Hebrew University of Jerusalem is an AAALAC international accredited institution.

Intraperitoneal Glucose Tolerance Test (IP-GTT)

A standard IP-GTT test was performed on mice after an overnight fast. Glucose in saline was injected intraperitoneally (1.5 g/kg body weight). Venous blood samples from small tail clips were taken for glucose determination using a glucometer (FreeStyle Freedom, Abbott Diabetes Care, Alamada, Calif.).

Statistical Analysis

Results are given as Mean±SEM. Statistical significance ($p<0.05$) was calculated among experimental groups using the two-tailed Student's t test.

Results and Discussion

The effects of the commercially available derivative of 1 (E)-2-amino-5-((E)-3-(5-nitrofuran-2-yl)allylidene)thiazol-4(5H)-one (2) were tested in cultured L6 myotubes (Scheme 1). It was found that 2 slightly increased the rate of glucose uptake in L6 myotubes and marginally induced Thr$^{172}$ phosphorylation in AMPK; however, these effects were observed only at high concentrations, above 500 µM (data not shown).

The effects of various other commercially available heterocyclic compounds that structurally related to 2 were tested as described above. These compounds were selected according to their structural similarity to (E)-5-allylidene-2-aminothiazol-4(5H)-one moiety in 2. Table 1 shows that 2-amino-5-ethylthiazol-4(5H)-one (3) increased Thr$^{172}$ phosphorylation in AMPK and augmented the rate of glucose uptake in L6 myotubes.

TABLE 1

Screening of compounds 3-12 (Values are expressed as Mean ± SD (n = 3).

| Compound | Structure | Effect on glucose uptake [100 μM] in L6 myotubes (%) | Phosphorylation of AMPK at Thr$^{172}$ |
|---|---|---|---|
| 3<br>2-amino-5-ethylthiazol-4(5H)-one | 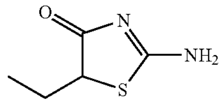 | 131.4 ± 6.8* | + |
| 5<br>2-amino-1,3,4-thiadiazole | 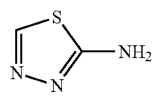 | 97.4 ± 2.9 | − |
| 6<br>2-amino-5-methyl-1,3,4-thiadiazole | 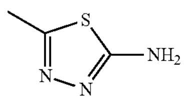 | 101.4 ± 5.5 | − |
| 7<br>3-mercapto-4-methyl-4H-1,2,4-triazole | 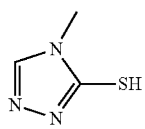 | 107.0 ± 7.5 | − |
| 8<br>2-mercaptopyrimidine | 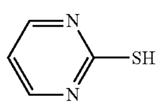 | 100.5 ± 4.9 | − |
| 9<br>2-mercapto-1-methylimidazole | 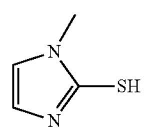 | 93 ± 9.5 | − |
| 10<br>2-aminothiazole | 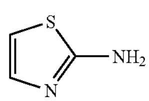 | 95.7 ± 5.1 | − |
| 11<br>2-mercapto-2-thiazoline | 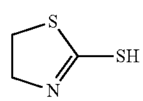 | 105.6 ± 6.8 | − |
| 12<br>2-amino-5-nitrothiazole | 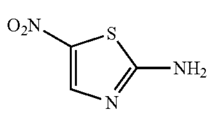 | 95.1 ± 8.9 | − |

FIG. 1 shows the time-course and dose-dependent analyses of these effects. As shown in FIG. 1, compounds 3, 4 and 15 increase the rate of glucose uptake in L6 myotubes by activating AMPK. FIG. 1 shown the time-course analysis of dGlc uptake in myotube cultures incubated with 3 (●), 4 (■) or 15 (◊) or DMSO (Δ). The cultures were then taken for the dGlc uptake assay. The basal rate of dGlc uptake at the beginning of the experiment (2.28±0.1 nmol/mg protein/min) was assigned the 100% value. Maximal glucose uptake stimulatory effect of 3 occurred within 5 hours [131.4%±6.8%, compared to vehicle (DMSO) treated control, FIG. 1A]. FIG. 1B shows a dose dependent study for the tested compounds. All cultures were incubated for 5 and 12 hours, then washed and taken for the standard [$^3$H]dGlc uptake assay. The basal rate of dGlc uptake at zero time (2.38±0.21 nmol/mg protein/min) was taken as 100%. FIG. 1B shows that the maximal effective concentration of the compound 3 was 100 μM. Above this concentration, 3 exhibited cytotoxic effects. Interestingly, as shown in FIG. 1C, the time-course analysis shows that the stimulatory effect of 3, after a peak at 5 hours, gradually declined to the basal level. Compound 3-induced Thr$^{172}$ phosphorylation in AMPK was maximal after 40 minutes of incubation and returned to the basal hypo-phosphorylated level after 3 hours. Whole cell lysates were prepared and Western blot analyses performed with antibodies against AMPKα and pTyr$^{172}$-AMPKα are shown in FIG. 1C. and the band densities are shown in FIG. 1D. Additional compounds were screened, (Table 2). Among these Compounds 4 and 15 also significantly induced AMPK phosphorylation and increased the rate of glucose uptake in L6 myotubes (172.4%±12.4% and 132.9%±13.8%, respectively, compared to DMSO-treated myotubes) (FIG. 1). The maximal effective concentration of both compounds (100 μM) was similar to that of 3, yet, their stimulatory effect on glucose uptake persisted for 24 hours (FIGS. 1A and 1B). This was accompanied by a stable Thr$^{172}$ phosphorylation of AMPK also up to 24 hours of incubation (FIGS. 1C and 1D).

TABLE 2

Screening of compounds 4-18 (Values are expressed as Mean ± SD (n = 3).

| Compound | Structure | Effect on glucose uptake [100 µM] in L6 myotubes (%) | Phosphorylation of AMPK at Thr$^{172}$ |
|---|---|---|---|
| 4 6-ethoxybenzo[d]thiazole-2-thiol | | 172.4 ± 12.4* | + |
| 13 benzothiazole | | 117.4 ± 9.7 | − |
| 14 6-ethoxybenzothiazol-2-amine | | 111.4 ± 14.2 | − |
| 15 6-bromo-2-benzothiazolinone | | 132.9 ± 13.8* | + |
| 16 1H-1,2,3-triazolo[4,5]pyridine | | 86.7 ± 17.9 | − |
| 17 1H-benzotriazole | | 87.5 ± 11.4 | − |
| 18 benzothiazol-2-amine | | 95.7 ± 5.1 | − |

Compound 4 was used for the design and synthesis of additional compounds. Initially, the effect of the ethoxy moiety in 4 on the biological activity was investigated: it was removed from the corresponding phenol alcohol derivatives following an overnight reaction with AlCl$_3$ in dichloroethane at room temperature, to obtain 2-mercaptobenzothiazol-6-ol (19), as described by Woltersdorf et al. (*J Med Chem*, 32 (1989) 2486-2492). When tested in the L6 myotube cultures, this compound did not stimulate the rate of glucose uptake, most likely due its substantial lower lipophilicity in comparison with the parent compound 4. In addition novel compounds, 20, 21, 22 and 23 were synthesized, and were assumed to be more lipophilic than 4 due to alkylation of the free thiol group. As shown in Scheme 2 above. This was obtained in the presence of a small excess of sodium hydride in dry THF. Interestingly, the alkylation occurred selectively on the thiol group of 19 and did not involve the unprotected phenol moiety. Compound 20 was shown to increase the rate of glucose uptake in L6 myotubes. Compound 22 was not stable during purification by column chromatography (e.g., silica gel or alumina). MS analysis conformed that 22 disintegrated during column chromatography. Thus, it was used in cell cultures right after its synthesis without additional purification.

Since the elimination of the ethyl moiety from the benzene ring in 4 abolished its biological activity, whether the free thiol group was alkylated or not, the former moiety was preserved in further syntheses. Thus, the free thiol group was replaced by various thioether functional groups to produce 24-29 (Scheme 2), which were more lipid soluble with an improved potential to penetrate cell membranes. Compounds 24 and 25 also contained a carboxylic acid moiety. The corresponding iodoalkyl or 3-chloroacetic/3-chloropropionic acids were reacted with the thiol group of 4 in the presence of a small excess of sodium hydride in dry THF. It was found that only the resulting compound 25 was biologically active; it activated AMPK and increased the rate of glucose uptake in L6 myotubes in a dose- and time-dependent manner. Specifically, 50 µM of 25 increased the glucose uptake 1.8-fold within 5 hours of incubation in comparison with the vehicle-treated cells. Thr$^{172}$ phosphorylation of AMPK in 25-treated myotubes peaked at 60 minutes of incubation (FIG. 2).

Figure 2A:
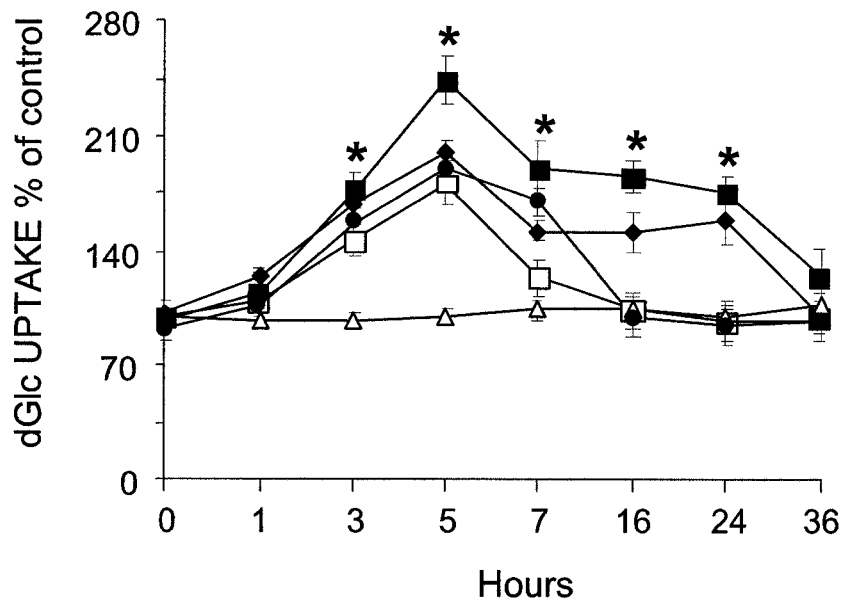
FIG. 2 shows that compounds 25, 31, 33 and 34 increase the rate of glucose uptake in L6 myotubes, FIG. 2A shown time-course analysis of dGlc uptake in L6 myotubes, where (□) 50 μM of 25, (●) 150 μM of 31, (◆) 100 μM of 33 or (■) 25 μM of 34, (Δ) control-vehicle (DMSO) only.
FIG. 2B shows a dose-response analysis in L6 myotubes incubated with increasing concentrations of 25 (□), 31 (●), 33 (◆), 34 (■) or the vehicle (Δ) for 5 hours.
FIG. 2C shows AMPK activation: L6 myotube cultures treated with the tested compounds, with. Representative blots are shown.
FIG. 2D shows a summary of the band density measurements of three independent experiments of Compound 24 (open bars), 31 (black bars), 33 (hatched bars) and 34 (bold hatched bars). *$p<0.05$, in comparison to the respective controls.
Figure 2B:
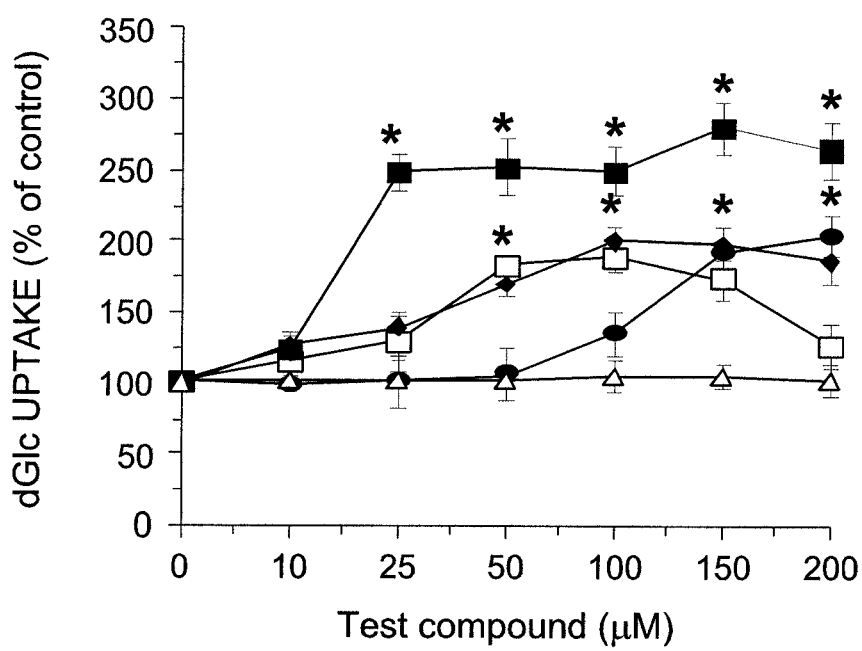

The basal rate of dGlc uptake at zero time (1.45±0.21 nmol/mg protein/min) was taken in FIG. 2A as 100%. The basal rate of dGlc uptake at zero time (1.49±0.15 nmol/mg protein/min) was taken as was taken in FIG. 2B as 100%. Similar to 22, compound 28 was also unstable during purification by column chromatography due to decomposition of the acetal group. Thus, it was used in the glucose uptake assay without purification.

Next, the thiol moiety in 4 was exchanged by sulfanilamide to produce 6-ethoxybenzothiazole-2-sulfonamide (30), using a two-step synthesis according to Woltersdorf et al. (*J Med Chem*, 32 (1989) 2486-2492). Briefly, compound 4 was treated with ammonium hydroxide (28%) and sodium hypochlorite (5.25%) in an aqueous solution and the corresponding sulfonamide derivatives were generated with 84% yield. The latter were oxidized with $KMnO_4$ in acetone/water (1:1) to yield 30. This compound was inactive in the glucose uptake assay in L6 myotubes. Further, compounds 31 and 32 were synthesized as shown in Scheme 2 using a novel synthetic method in which the corresponding thiol was refluxed overnight in the presence of HCl in THF to obtain 31. In this compound, two molecules of 4 were covalently bound by an S—S bond. Two 1H-benzoimidazole-2-thiol molecules were coupled under similar reaction conditions to obtain 32. In contrast to 31, the atoms in the benzothiazole moiety of 32 were replaced with nitrogen atoms following the deletion of the ethoxy moiety on the benzene ring. Compound 32 had no stimulatory effect on glucose uptake in L6 myotubes. However, as shown in FIG. 2, 31 substantially increased the rate of uptake in L6 myotubes: its maximal effect (189.0±21.8%, compared with a non-treated control) was obtained at 150 μM within 5 hours of incubation. This compound also induced $Thr^{172}$ phosphorylation in AMPK within 40 minutes of incubation, and this effect persisted up to 5 hours (FIG. 2). These effects seem to reflect the high lipophilicity of 32 and subsequently efficient permeability through the cell membrane. It is also assumed the S—S bond in 31 is cleaved intracellularly to release 4.

Figure 2C:
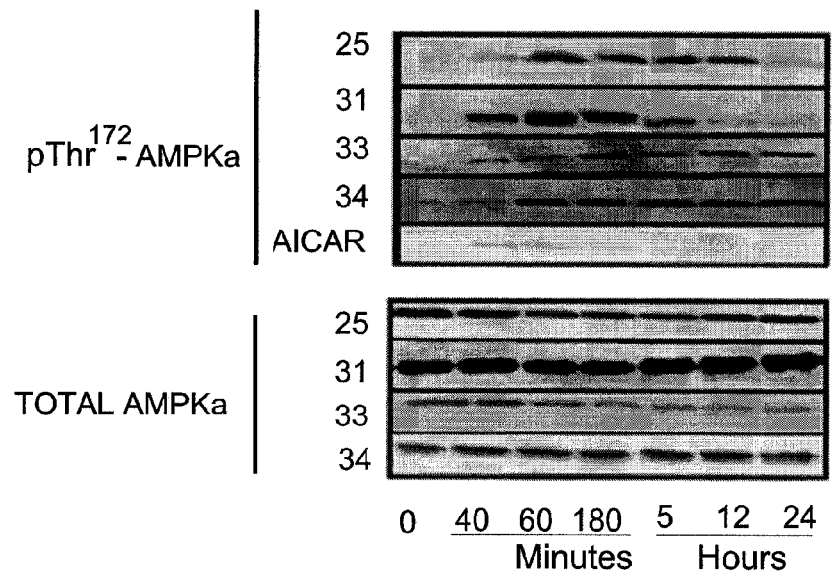
Figure 2D:
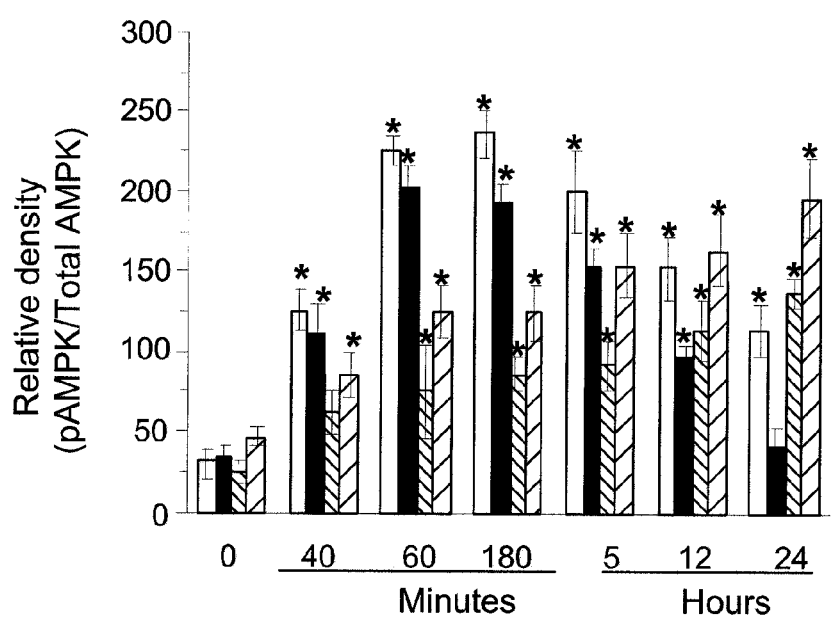

In addition, two related thioethers derivatives were synthesized. Compound 33 was obtained by coupling propylamine hydrochloride with 24, using 1-ethyl-3-(3-dimethyllamino-propyl)carbodiimide hydrochloride (EDC)/hydroxybenzotriazole (HOBt) and triethylamine in THF [19]. Compound 34 was synthesized in a two-step procedure. First, commercially available 2-methylbenzothiazole was transformed into 2-(chloromethyl)benzothiazole intermediate by chlorination (trichloroisocyanuric acid was used for selective chlorination of a methyl group). The resulting 2-(chloromethyl)benzothiazole was then condensated with 4, using a di-iso-propylethyl amine catalysis in dry THF. FIG. 2 shows that both compounds markedly augmented the rate of glucose uptake in L6 myotubes, although the lipophilic amide derivative 33 was somewhat less potent and less effective than benzothiazol derivative 34: 100 μM of the former increased 2-fold the rate of glucose uptake in L6 myotubes within 5 hours of incubation, compared to the 2.5-fold increase 34 induced under similar experimental conditions. Moreover, the minimal effective concentration of 34 was 25 μM and its stimulatory effect remained unaltered up to 24 hours. The time course of $Thr^{172}$ phosphorylation of AMPK induced by 33 and 34 varied: the amide derivative 33 induced significant $Thr^{172}$ phosphorylation after 5 hours of incubation whereas 34 caused it already within 1 hour (FIGS. 2C and D). This temporal difference may be explained by a slower rate of the intracellular cleavage of the amide bond in comparison to the more stable thioether bond.

The effect of 34 on the rate of glucose uptake in L6 was tested in the absence or the presence of the insulin. FIG. 3 shows that the effect of 34 on GLUT-4 translocation to the plasma membrane of L6 myotubes is by a non-insulin dependent manner.

Figure 3A:
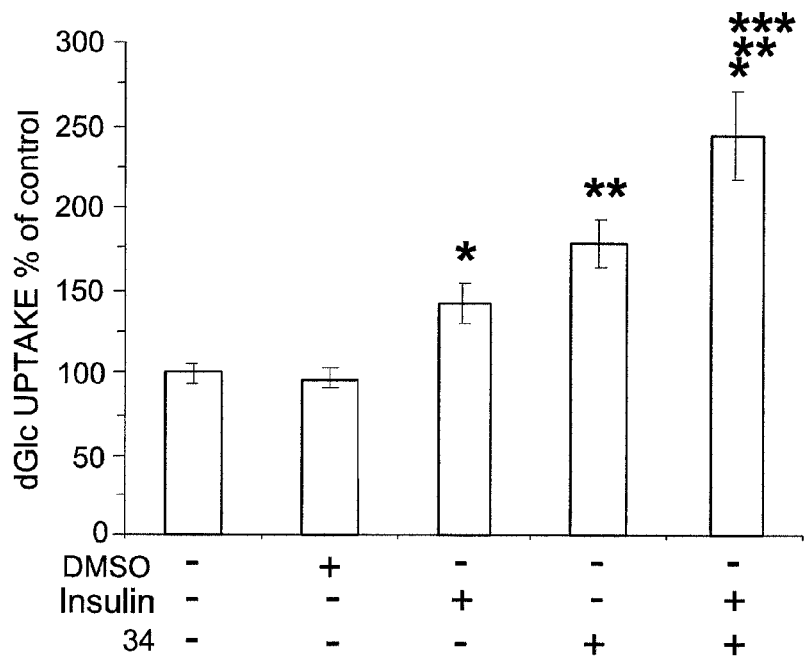
FIG. 3A shows the relative rates of glucose uptake in L6 myotubes in the presence of 34 and insulin: $p<0.05$ in comparison with the DMSO control. *$p<0.05$ in comparison with 34- or insulin-treated myotubes.

As shown in FIG. 3A, L6 myotube cultures were washed and received serum free-MEM with 0.5% of BSA, containing 23.0 mM D-glucose and incubated for 9 hours. During the last 5 hours of incubation the cells received 25 μM of 34 or the vehicle DMSO (0.1% v/v). Insulin (100 nM) was introduced during the last 20 minutes of incubation. The basal rate of the dGlc uptake (1.62±0.1 nmol/mg protein/min) was taken as 100%. FIG. 3A confirms that 34 was active in the absence of insulin. It also shows that this stimulatory effect was additive to effect of insulin when both agents were present together: insulin and 34 increased the rate of glucose uptake by 45%±13% and 75%±17%, respectively, while their combined effect reached 148%±29%. These findings suggest that the mechanisms of action of 34 and insulin may be distinct.

Figure 3B:
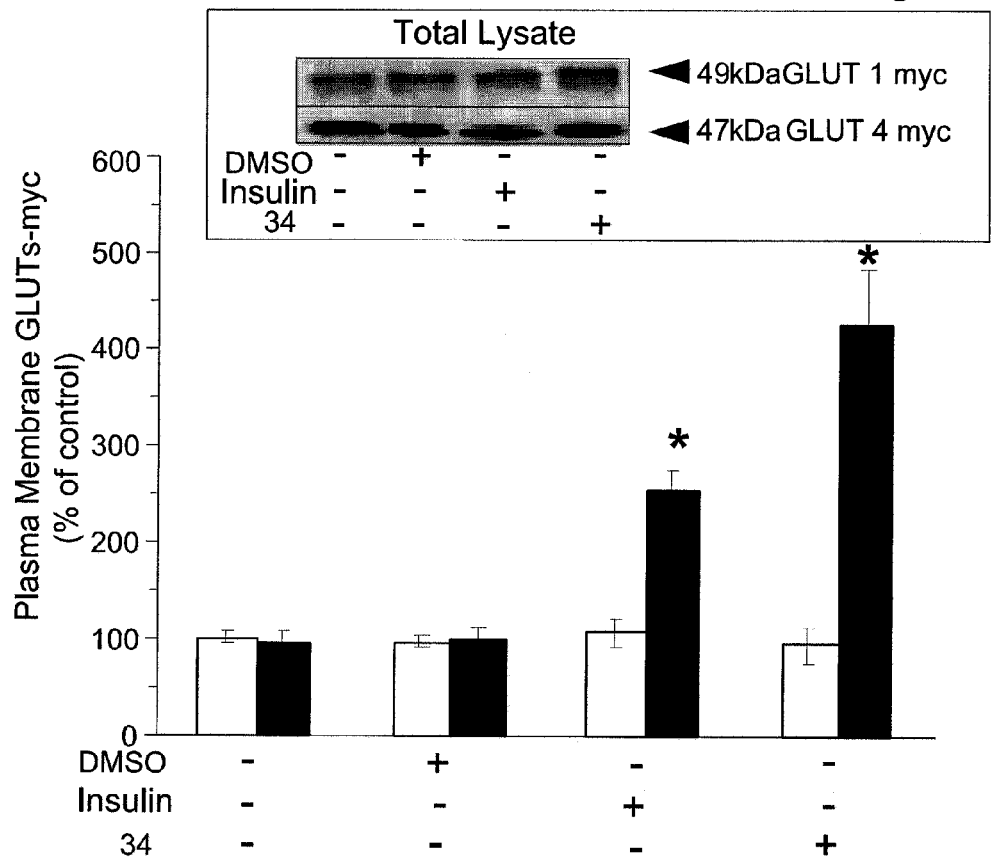
FIG. 3B shows that compound 34 induces GLUT-4, but not GLUT-1 translocation to the plasma membrane of L6 myotubes. *$p<0.05$ in comparison with the respective control. Inset: a representative Western blot depicts the content of the corresponding glucose transporters in lysates prepared from normal L6 myotubes that were treated as described above.

The capacity of compound 34 to increase the rate of glucose uptake by increasing GLUT4 content in the plasma membrane of myotubes was tested. FIG. 3B shows that both insulin and 34 increased the abundance of GLUT4myc, but not GLUT1myc, in the plasma membrane of L6 myotubes. The cells expressing GLUT1myc or GLUT4myc were treated with 25 μM of 34 or DMSO as described above. At the end of the incubation, the cultures were taken for immunodetection of surface GLUT1myc (open bars) or GLUT4myc (black bars), as described herein above.

The effect of insulin on the GLUT4myc translocation to the plasma membrane of myotubes was very fast (30 min) compared to the 5 hour period required for 34 to exert its action. Neither compound altered the total content of GLUT1 or GLUT4 in myotubes, as determined in whole cell lysates of treated L6 myotubes (insert, FIG. 3B).

Since both insulin and 34 induced GLUT4 translocation to the plasma membrane, albeit with different time courses, it was further tested whether 34 employed the insulin transduction mechanism. Therefore, inhibitors of the insulin transduction pathways, the PI3K inhibitor wortmannin, and an Akt/PKB inhibitor (1,3-Dihydro-1-(1-((4-(6-phenyl-1H-imidazo[4,5-g]quinoxalin-7-yl)phenyl)methyl)-4-piperidinyl)-2H-benzimidazol-2-one tri-fluoroacetate salt hydrate) were used in 34-treated cells.

Cells were incubated in the absence or presence of 100 nM of wortmannin or 100 nM of the Akt/PKB inhibitor. These inhibitors were added 30 min prior to the addition of 34 or insulin to the cultures. The basal rate of the dGlc uptake (2.32±0.12 nmol/mg protein/min) in myotubes exposed to 23 mM D-glucose with DMSO was taken as 100%.

Figure 3C:
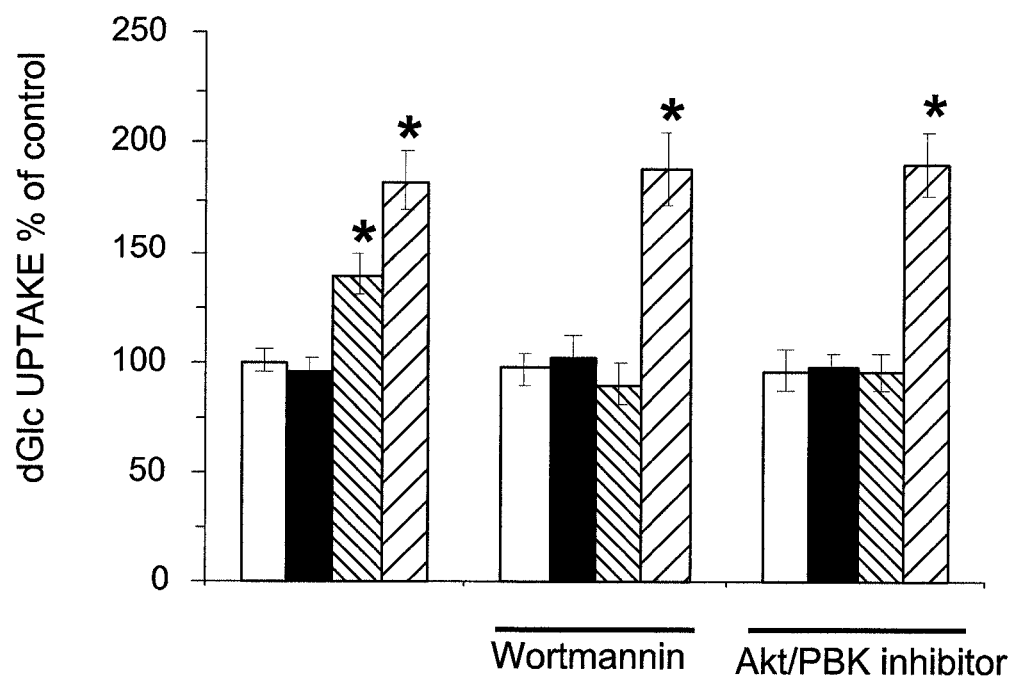
FIG. 3C shows that compound 34 augments the rate of glucose transport in a PI3K- and Akt/PKB-independent manner: control L6 myotubes (open bars) or myotubes treated as described above with 34 (gray bars), insulin (hatched bars) or the vehicle (black bars), *$p<0.05$, in comparison with the respective controls.

Both inhibitors suppressed insulin-stimulated glucose uptake in L6 myotubes (FIG. 3C). However, the stimulatory effect of 34 on glucose uptake remained unaltered in the presence of both inhibitors, suggesting that the insulin transduction mechanism is not involved in mediating 34-induced translocation of GLUT4.

Figure 4A:
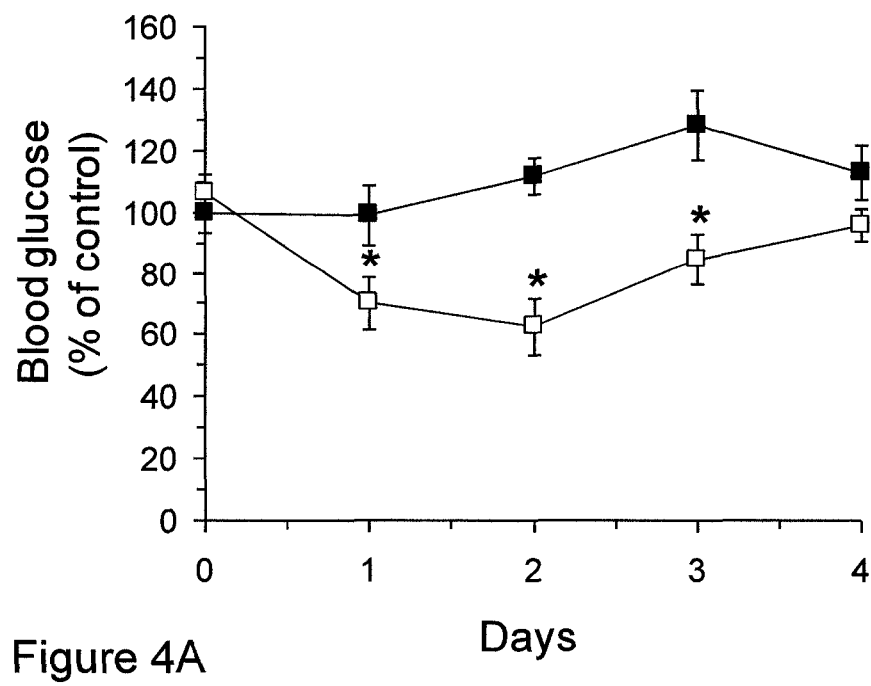
FIG. 4A shows the effect of 34 on the blood glucose level: hyperglycemic KKAy mice were injected s.c. twice daily with sesame oil (150 μl, ■) or 34 (75 mg/kg body weight, □) for 4 days and blood glucose was measured at the indicated times.
Figure 4B:
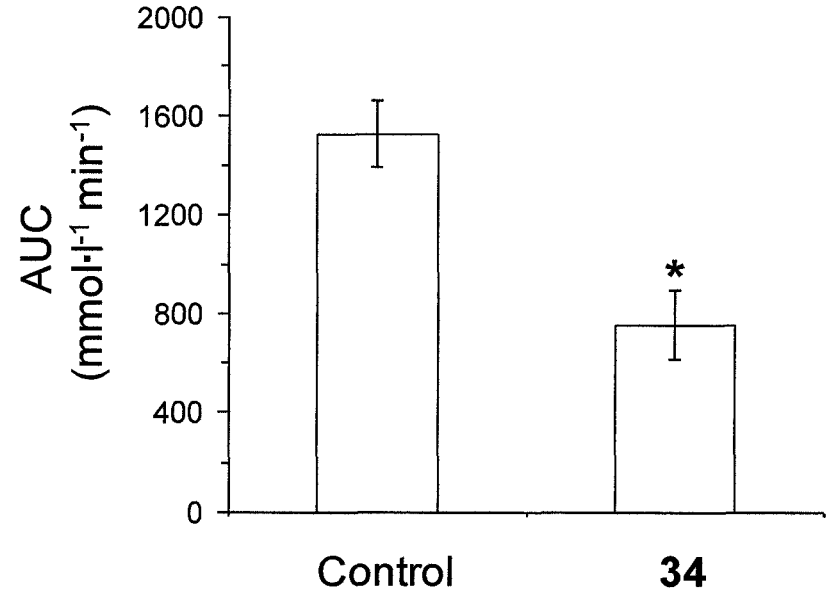
FIG. 4B shows that compound 34 improved glucose tolerance in hyperglycemic KKAy mice: Mean±SEM, n=10, *$p<0.05$ in comparison with the oil-treated group.
Figure 5:
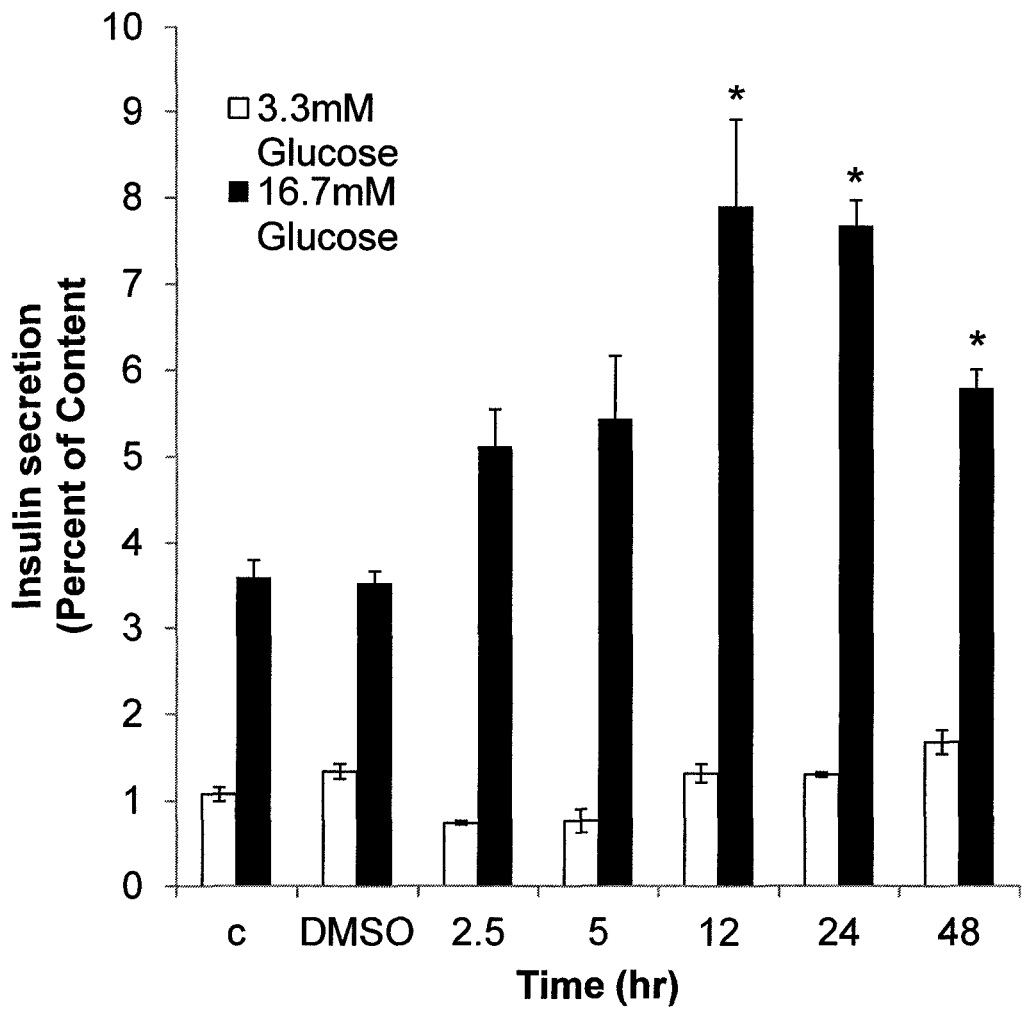
FIG. 5 is a bar graph showing that EMM-45 (Compound 20 in Scheme 2) augments glucose-stimulated insulin secretion from INS-1E cells. The results are given as percent secreted insulin of the total insulin content in the cells. Vehicle (DMSO)-treated cells were taken to the glucose-stimulated insulin secretion (GSIS) assay following 48 h incubation. Results are mean±SEM, n=4, P>0.05 in comparison with the vehicle-treated cells.

The antihyperglycemic potential of 34 was investigated in an animal model of diabetes. Test compound was injected subcutaneously (75 mg per kg body weight, suspension in sesame oil, twice daily) to diabetic KKAy mice; control mice received the vehicle only. The blood glucose levels at day zero, 20.8±0.9 and 22.3±1.3 mM for the control and 34-treated groups, respectively, were taken as the reference 100% values in FIG. 4A. This Figure shows that 34 significantly reduced blood glucose nearly by nearly 30%, 45% and 50% on days 1, 2 and 3 of treatment, respectively, whereas the oil treatment (vehicle) had no effect. It should be noted, however, that despite the marked antihyperglycemic effects of 34, normoglycemia was not reached. To better evaluate the potential of 34, the glucose tolerance of treated KKAy mice was evaluated using a standard IP-GTT. The mice were treated with 34 as described above for two days, after which IP-GTT was performed after an overnight fast, as described [6]. FIG. 4B shows that glucose tolerance was significantly improved in the treated mice: the corresponding areas under the curve (AUC) were 1523.9±132.9 vs. 753.6±142.2 mmol glucose/l/min for oil- and 34-treated KKAy mice, respectively. These results show that 34 improved total body glucose clearance in diabetic KKAy mice by 40%-50% following a two-day treatment. IP-GTT was performed following an overnight fast in mice treated with 34 or oil, as described herein above. As shown in FIG. 5, compound 20 was increased the glucose stimulated insulin secretion in INS-1E. The cells were grown in standard RPMI1640 complete culture medium, treated with 10 µM compound 20 and incubated for the indicate time periods. At the end of incubations the cells were taken for a standard GSIS assay described herein.

Figure 6:
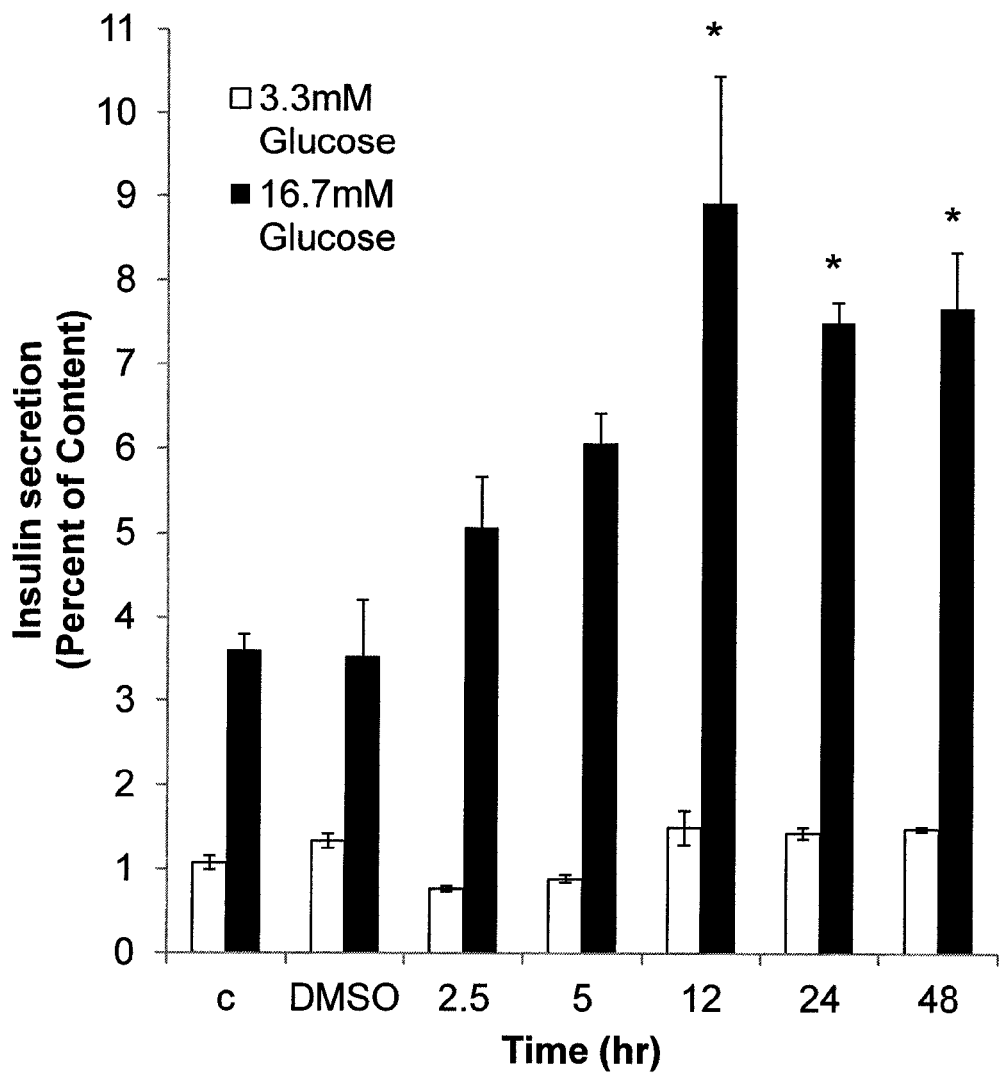
FIG. 6 is a bar graph showing that EMM-45 (compound 20) augments glucose-stimulated insulin secretion from INS-1E cells. Results are mean±SEM, n=4, P>0.05 in comparison with the vehicle-treated cells.
Figure 7:
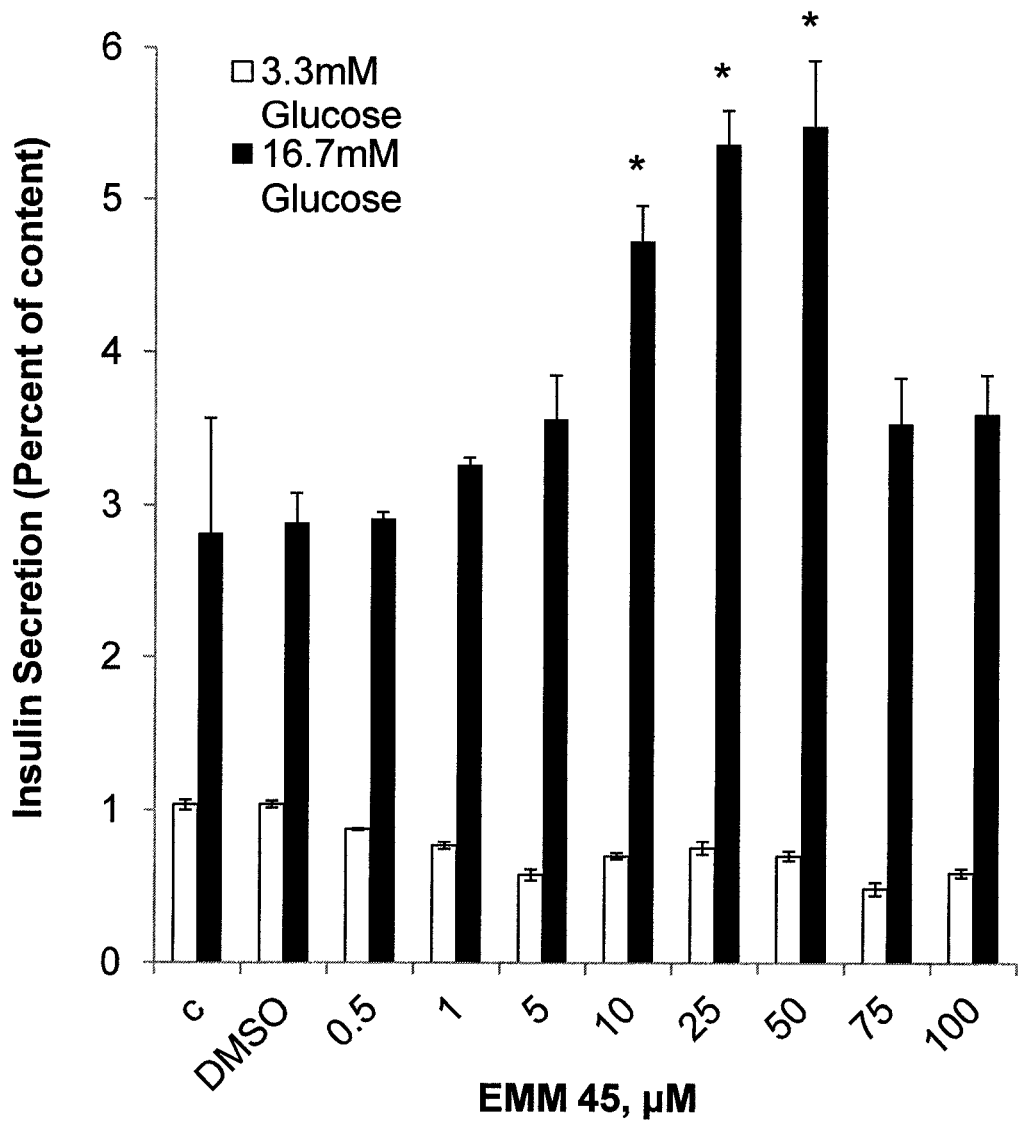
FIG. 7 is a bar graph showing a dose-response analysis of EMM-45 (compound 20)-induced insulin secretion from INS-1E cells. Results are mean±SEM, n=4, P>0.05 in comparison with the vehicle-treated cells.

FIG. 6 also supports the previous studies and shows that treating INS-1E cells with 25 µM EMM-45 increased the glucose-stimulated insulin secretion. FIG. 7 shows a dose response assay with different concentrations of EMM-45 (compound 20) incubated for 5 h.

Figure 8:
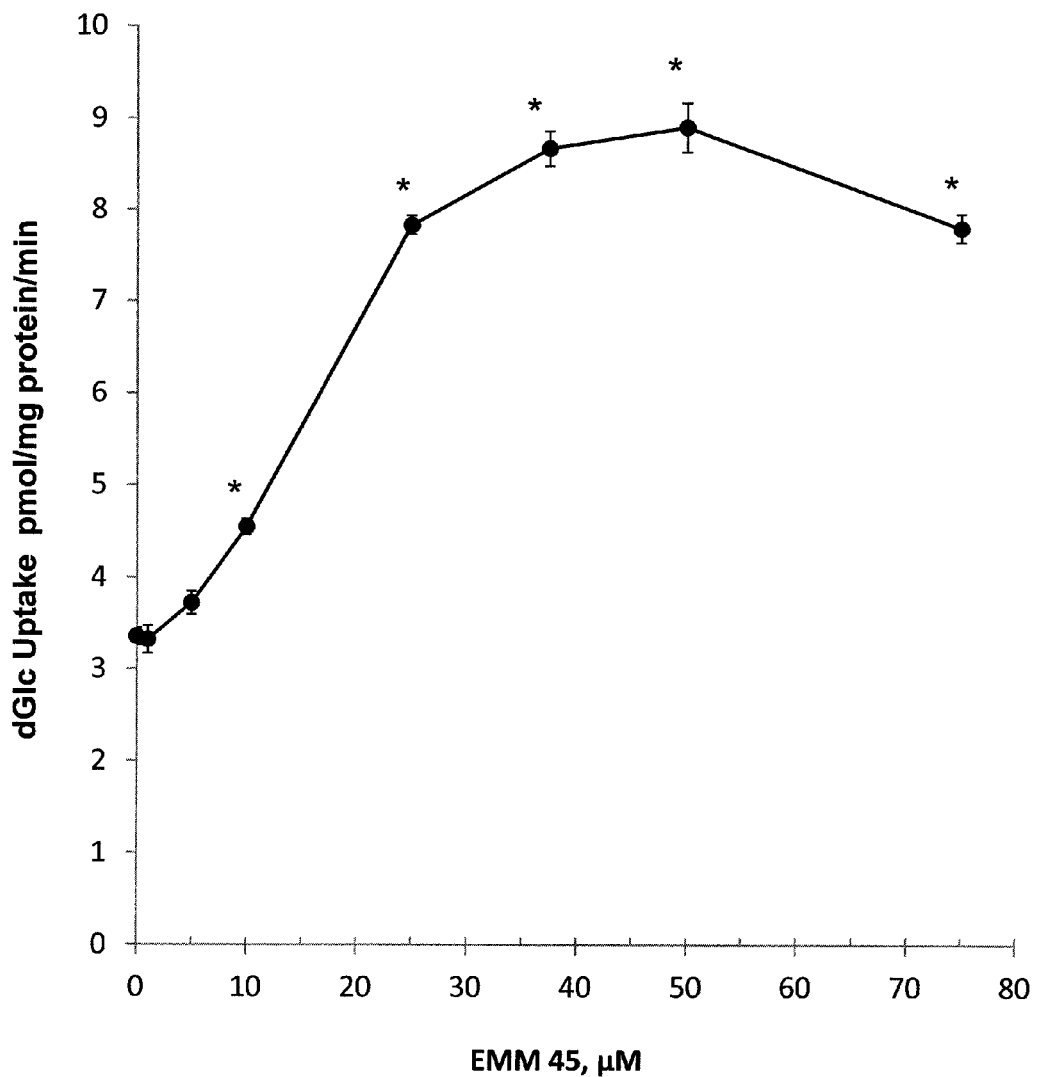
FIG. 8 is a graph showing that EMM-45 (compound 20) increases the rate of glucose uptake in L6 myotubes. Results are given as pmol 2-deoxy-D-glucose per mg protein per min Results are mean±SEM, n=3, P>0.05 in comparison with the vehicle-treated cells.

As shown in FIG. 8, EMM-45 (compound 20) induced an increase in the rate of glucose uptake in L6 myotubes in a dose dependent manner. Cultured L6 myotubes were incubated with the indicated concentrations of EMM-45 for 5 h, and then washed and taken for the standard [$^3$H]-2-deoxy-D-glucose uptake assay.

Figure 9:
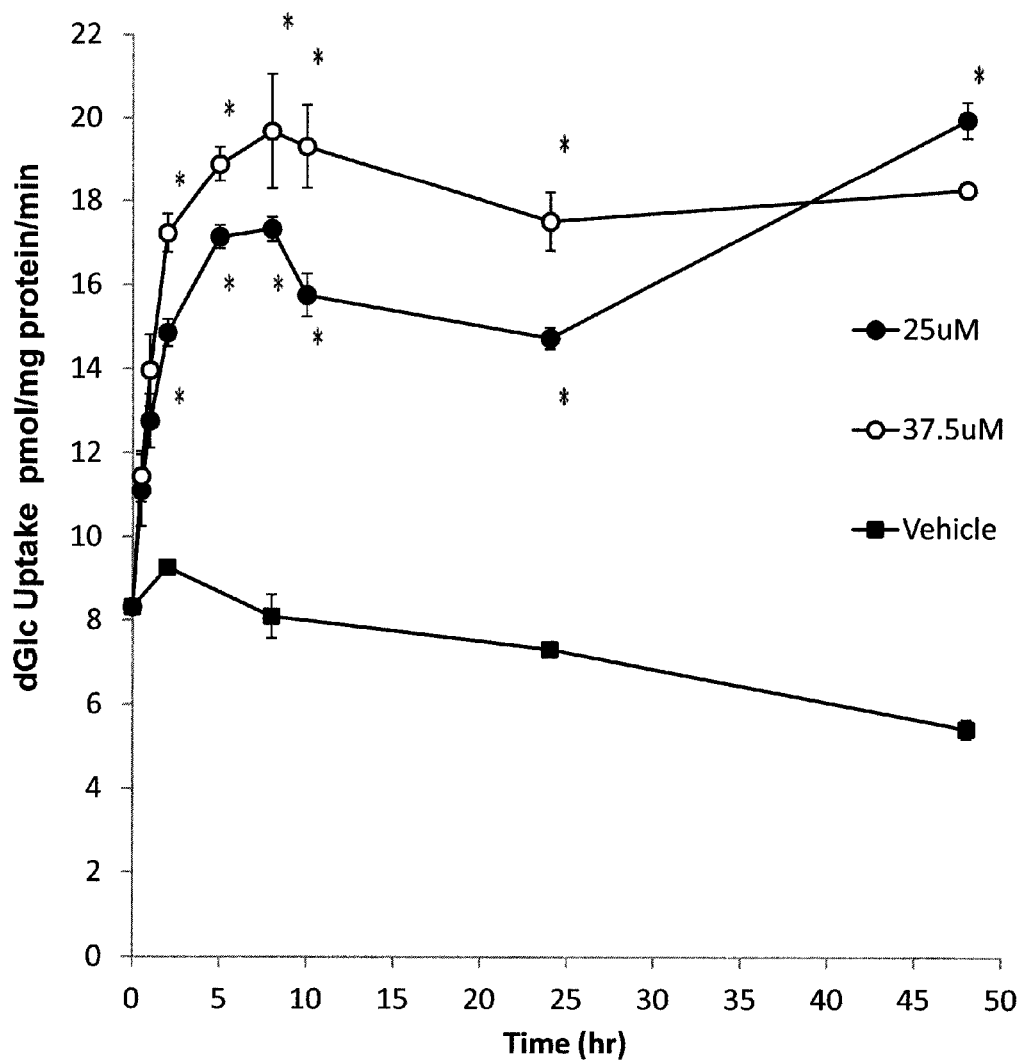
FIG. 9 is a graph showing time course analysis of EMM-45 effect on glucose transport in L6 myotubes. Results are given as pmol 2-deoxy-D-glucose per mg protein per min Results are mean±SEM, n=3, P>0.05 in comparison with the vehicle-treated cells.

As further shown in FIG. 9, EMM-45 (compound 20) induces stimulation of glucose uptake in L6 myotubes.

Figure 10:
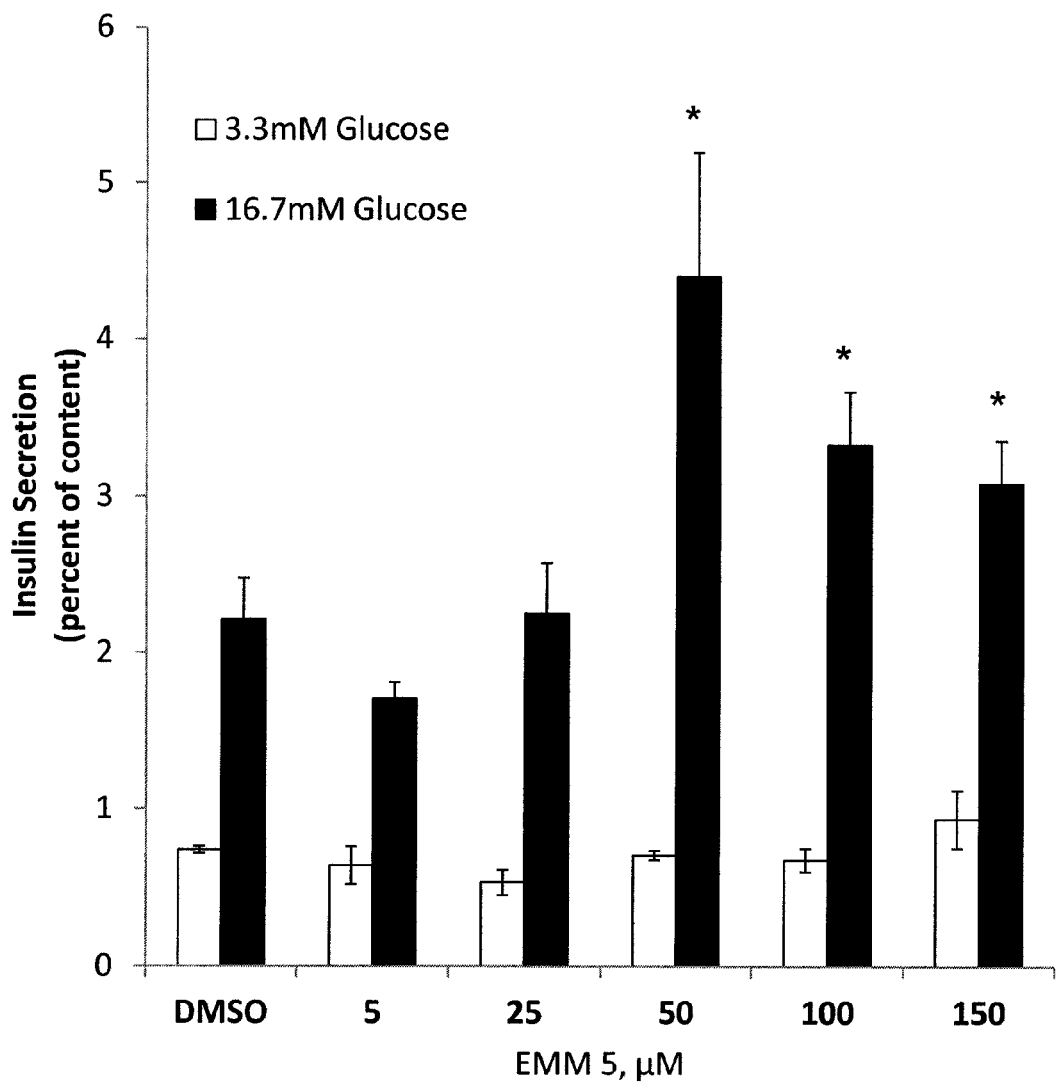
FIG. 10 is a bar graph showing that EMM-5 (compound 31 in Scheme 2) increases glucose-stimulated insulin secretion from INS-1E cells. Results are mean±SEM, n=4, P>0.05 in comparison with the vehicle-treated cells.
Figure 11:
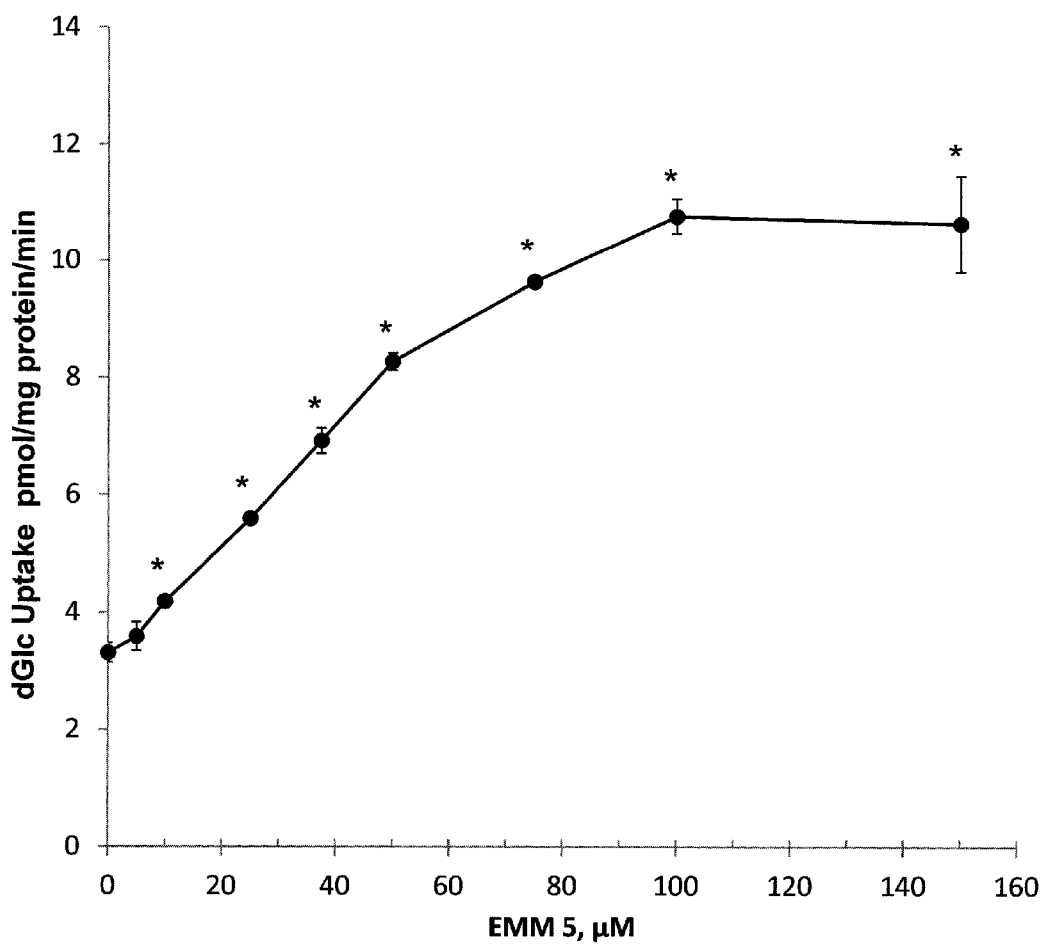
FIG. 11 is a graph showing that EMM-5 increases the rate of glucose uptake in L6 myotubes. Cultured L6 myotubes were incubated with the indicated concentrations of EMM-5 for 5 h, and then washed and taken for the standard [$^3$H]-2-deoxy-D-glucose uptake assay. Results are given as pmol 2-deoxy-D-glucose per mg protein per min Results are mean±SEM, n=3, P>0.05 in comparison with the vehicle-treated cells.
Figure 12:
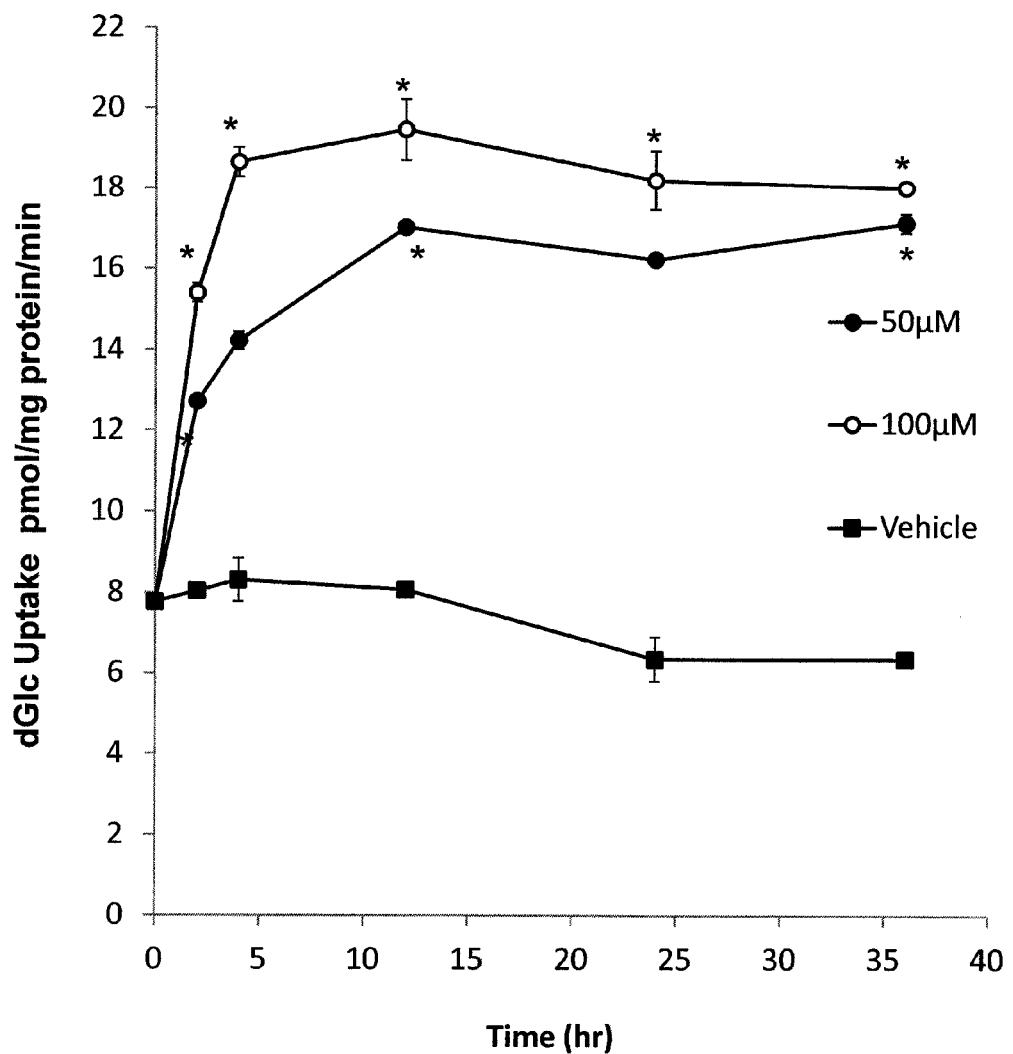
FIG. 12 is a graph showing the time course analysis of EMM-5-induced stimulation of glucose uptake in L6 myotubes. Cultured L6 myotubes were incubated with the indicated concentrations of EMM-5 or the vehicle (DMSO) for the indicated time periods. The cultures were then washed and taken for the standard [$^3$H]-2-deoxy-D-glucose uptake assay. Results are given as pmol 2-deoxy-D-glucose per mg protein per min Results are mean±SEM, n=3, P>0.05 in comparison with the vehicle-treated cells.

FIG. 10 shows that EMM-5 (compound 31) increases glucose-stimulated insulin secretion from INS-1E cells. INS-1E cells were grown in standard RPMI1640 complete culture medium, treated with the indicated concentrations of EMM-5 and incubated for 5 h. At the end of incubations the cells were taken for a standard GSIS assay and the results are given as percent secreted insulin of the total insulin content in the cells. Vehicle (DMSO)-treated cells were taken to the GSIS assay following 48 h incubation. FIG. 11 shows that EMM-5 (compound 31) increases the rate of glucose uptake in L6 myotubes. FIG. 12 shows a time course analysis.

CONCLUSIONS

Various substituted benzothiazol derivatives were synthesized and screened for their potential anti-hyperglycemic activity. The ethoxybenzothiazole moiety in 34 was found to be a critical motive required for the augmentation of glucose transport in L6 myotubes and the activation of AMPK. This study shows that ethoxybenzothiazole derivatives in general and 34 in particular, may represent a new class of compounds for the development of novel antidiabetic drugs. Compound 34 augments the rate of glucose uptake at pharmacologically relevant concentrations (25 µM). This compound also significantly decreased the blood glucose level in an animal model of T2DM (KKAy mice) and improved whole body glucose disposal. The stimulating effect of 34 in L6 myotubes is correlated to the activation of AMPK and an increased abundance of GLUT-4 in the myotube plasma membrane, without engaging the insulin transduction mechanism in the process. These properties make 34 a prototype molecule for the development of a unique class of antidiabetic drugs. In addition some derivatives (e.g., EMM-45) exert dual functions: they increase the rate of glucose transport in L6 myotubes and augment glucose-stimulated insulin secretion from INS-1E β-cell. These properties make these compounds unique in modern strategies for pharmacotherapy of type II diabetes.

The invention claimed is:
1. A compound of formula (II):

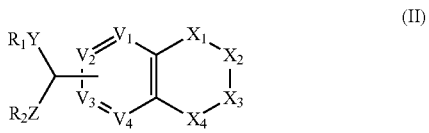

wherein
$X_1, X_2, X_3$ and $X_4$ are each independently selected from the group consisting of S, O, $CH_2$, $CHR_3$, NH and $NR_3$; provided that at least one of $X_1$ to $X_4$ is O or S and at least one of $X_1$ to $X_4$ is $CHR_3$;
$V_1, V_2, V_3$ and $V_4$ are each independently selected from N, C, CH and $CR_4$;
Y and Z are each S;
$R_1$ and $R_2$ are each independently selected from straight or branched $C_1$-$C_{20}$ alkyl, straight or branched $C_2$-$C_{20}$ alkenyl and straight or branched $C_2$-$C_{20}$ alkynyl, each optionally interrupted with at least one NH; or wherein $R_1$ and $R_2$ together with Y, Z and the carbon atom connecting them form a 5 to 10 membered ring; optionally substituted by at least one group selected from straight or branched $C_1$-$C_{10}$ alkyl, straight or branched $C_2$-$C_{10}$ alkenyl and straight or branched $C_2$-$C_{10}$ alkynyl;
$R_4$ is selected from the group consisting of halogen, straight or branched $C_1$-$C_{20}$ alkyl, straight or branched $C_2$-$C_{20}$ alkenyl and straight or branched $C_2$-$C_{20}$ alkynyl;
$R_3$ is selected from the group consisting of straight or branched $C_1$-$C_{12}$ alkyl, straight or branched $C_2$-$C_5$ alkenyl, straight or branched $C_2$-$C_5$ alkynyl, —COOH, $C_1$-$C_8$ alkoxy, $C_1$-$C_5$ amidyle, $C_1$-$C_5$ carboxyl, $C_6$-$C_{12}$ aryl, $C_4$-$C_{12}$ heteroaryl and heterocyclyl, wherein each of aryl, heteroaryl and heterocyclyl is optionally substituted by at least one of alkoxy, alkyl, alkenyl, alkynyl, amino, cyano, halogen, and 1,3-dithian-benzyl.
2. A compound of claim 1, wherein at least one of $X_1$ to $X_4$ is O.
3. A compound of claim 1, wherein at least two of $X_1$ to $X_4$ are O.
4. A compound of claim 1, wherein $R_3$ is aryl or heteroaryl.
5. A compound of claim 1 of formula (III):

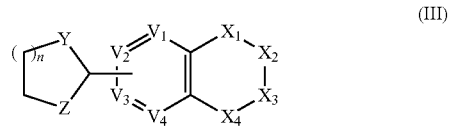

wherein $X_1$ to $X_4$, $V_1$ to $V_4$, Y, Z and $R_1$ to $R_4$ are as defined in claim 1; and n is 1 to 5.
6. A medicament comprising the compound of claim 1 and a pharmaceutically acceptable carrier or auxiliary.
7. A method of treating elevated blood glucose levels in a subject in need thereof, said method comprising administering to said subject a compound of claim 1.
8. A method for the treatment of at least one condition selected from hyperglycemia, diabetes, altered insulin secretion, insulin resistance, obesity and metabolic syndrome X;

said method comprising administering to a subject in need thereof an effective amount of a compound according to claim 1.

9. A method according to claim 8, wherein said condition is diabetes.

\* \* \* \* \*